(12) United States Patent
Anderson et al.

(10) Patent No.: US 7,700,646 B2
(45) Date of Patent: Apr. 20, 2010

(54) COMPOUNDS FOR USE IN THE TREATMENT OF INFECTION

(75) Inventors: James C. Anderson, Nottingham (GB); Catherine Headley, Leeds (GB); Paul D. Stapleton, London (GB); Peter W. Taylor, Billingshurst (GB)

(73) Assignee: The University of London, School of Pharmacy, London (GB)

( * ) Notice: Subject to any disclaimer, the term of this patent is extended or adjusted under 35 U.S.C. 154(b) by 887 days.

(21) Appl. No.: 11/455,889

(22) Filed: Jun. 20, 2006

(65) Prior Publication Data

US 2007/0021384 A1  Jan. 25, 2007

Related U.S. Application Data

(63) Continuation-in-part of application No. PCT/GB2005/002670, filed on Jul. 6, 2005.

(30) Foreign Application Priority Data

Jul. 6, 2004  (GB) ................. 0415181.7

(51) Int. Cl.
A61K 31/353 (2006.01)
C07D 311/60 (2006.01)
C07D 311/62 (2006.01)

(52) U.S. Cl. .................. 514/456; 549/399; 549/404

(58) Field of Classification Search ............. 549/404, 549/399; 514/456
See application file for complete search history.

(56) References Cited

U.S. PATENT DOCUMENTS

| 6,696,485 | B1 | 2/2004 | Romanczyk, Jr. et al. |
| 7,109,236 | B2 * | 9/2006 | Zaveri et al. ............ 514/456 |
| 7,358,383 | B2 * | 4/2008 | Dou et al. ............... 560/61 |
| 2004/0186167 | A1 | 9/2004 | Ping et al. |

FOREIGN PATENT DOCUMENTS

| CN | 1041375 | 9/1988 |
| EP | 0 397 914 | 11/1990 |
| WO | WO 03/101927 | 12/2003 |
| WO | WO 2004/052873 | 6/2004 |
| WO | WO 2005/034976 | 4/2005 |

OTHER PUBLICATIONS

Chemical Abstracts Registry No. 82540-88-3, Chem. Abstracts vol. 97:84389 (1982).*
Chemical Abstracts Registry No. 3143-32-6 (1984).*
Anderson et al., "Synthesis and antibacterial activity of hydrolytically stable (−)-epicatechin gallate analogues for the modulation of β-lactam resistance in *Staphylococcus aureus*", Bioorganic & Medicinal Chemistry Letters, pp. 2633-2635, 2005.
Wan et al., "Enantioselective synthesis of afzelechin and epiafzelechin", Tetrahedron, pp. 8207-8211, 2004.
Kazi et al., Anticancer Research (abstract only), pp. 1-3, 2004.
Wan et al., "Study of the green tea polyphenols catechin-3-gallate (CG) and epicatechin-3-gallate (ECG) as proteasome inhibitors", Bioorganic & Medicinal Chemistry, pp. 3521-3527, 2004.
Kato et al., Synlett, (abstract only), 2001.
Caturla et al., "The Relatsionship between the Antioxidant and the Antibacterial Properties of Galloylated Catechins and the Structure of Phospholipid Model Membranes", Free Radical Biology & Medicine, vol. 34, No. 6, pp. 648-662, 2003.
Hamilton-Miller et al., "Disorganization of Cell Division of Methicillin-resistant *Staphylococcus aureus* by a component of tea (Camellia sinensis): a study by electron microscopy", FEMS Microbiology Letters, 176, pp. 463-469, 1999.

(Continued)

*Primary Examiner*—Bernard Dentz
(74) *Attorney, Agent, or Firm*—Fish & Associates, PC

(57) ABSTRACT

There is provided a novel compound of the general formula I

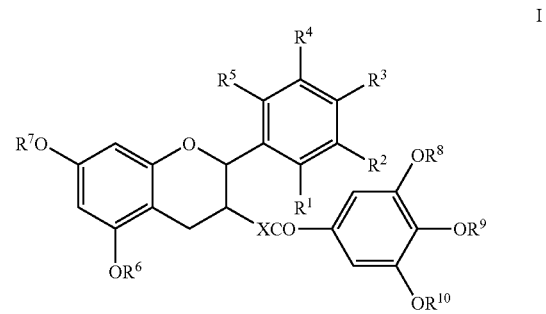

in which each of $R^8$ to $R^{10}$ is hydrogen, aryl, $C_{1-6}$ alkyl, trialkylsilyl or acyl; $R^1$ to $R^5$ are individually selected from hydrogen, hydroxy, $C_{1-6}$ alkoxy and acyloxy; $R^6$ and $R^7$ are H, $C_{1-4}$ alkyl, trialkylsilyl or acyl; X is O or NR, and R is H or Me; in which any of the alkyl groups including alkyl groups in alkoxy, acyl and acyloxy groups may be substituted by aryl, $C_{1-4}$ alkyl, $C_{1-4}$ alkoxy, hydroxyl, trialkylsiloxy or acyloxy groups; with the proviso that $R^2$ and $R^3$ are not both OH when $R^4$ is H or OH, $R^1$ and $R^5$ are both H, and X is O. The amide compounds (X is NR) are analogues of epigallocatechin gallate or epicatechin galate, with an amide bond in place of the natural ester bond, with resistance to hydrolysis by esterase enzymes. The ester compounds (X is O) have a different hydroxylation pattern on the B ring as compared to the natural products. The compounds may be used to modulate the resistance to β-lactam antibiotics of various infections, especially methicillin resistant *Staphylococcus aureus* (MRSA). Pharmaceutical compositions containing the novel compounds and combinations of the novel compounds and β-lactam antibiotics are described.

28 Claims, No Drawings

OTHER PUBLICATIONS

Hashimoto et al., "Interaction of Tea Catechins with Lipid Bilayers Investigated with Liposome Systems", Biosci. Biotechnol. Biochem, 63(12), pp. 2252-2255, 1999.

Kajiya et al., "Steric Effects on Interaction of Tea Catechins with Lipid Bilayers", Biosci. Biotechnol. Biochem., 65 (12), pp. 2638-2643, 2001.

Kajiya et al., "Effects of External Factors on the Interaction of Tea Catechins with Lipid Bilayers", Biosci. Biotechnol. Biochem., 66 (11), pp. 2330-2335, 2002.

Kohri et al., "Metabolic Fate of (-)-[44-$^3$H]Epigallocatechin Gallate in Rats after Oral Administration", J. Agric. Food Chem., 49, pp. 4102-4112, 2001.

Nakayama et al., "Affinity of Antioxidative Polyphenols for Lipid Bilayers Evaluated with a Liposome System", Biosci. Biotechnol. Biochem., 62 (5), pp. 1005-1007, 1998.

Stapleton et al., "Methicillin Resistance in *Staphylococcus aureus*: Mechanisms and Modulation", Science Progress, 85 (1), pp. 57-72, 2002.

Stapleton et al., "Modulation of β-lactam resistance in *Staphylococcus aureus* by catechins and gallates", International Journal of Antimicrobial Agents, 23 (5), pp. 462-467, 2004.

Yam et al., "Microbiological activity of whole and fractionated crude extracts of tea (Camellia sinensis), and of tea components", FEMS Microbiology Letters 152, pp. 169-174, 1997.

Yam et al., "The effect of a component of tea (Camellia sinensis) on methicillin resistance, PBP2' synthesis, and β-lactamase production in *Staphylococcus aureus*", Journal of Antimicrobial Chemotherapy, 42, pp. 211-216, 1998.

Yamashita et al., "Successful Green Tea Nebulization Therapy for Subglottic Tracheal Stenosis due to MRSA Infection", J. Infect., 42, pp. 222-223, 2001.

* cited by examiner

COMPOUNDS FOR USE IN THE TREATMENT OF INFECTION

CROSS-REFERENCE TO RELATED APPLICATION

This application is a continuation-in-part of PCT/GB2005/002670, filed Jul. 6, 2005, the entire disclosure of which is incorporated herein by reference.

BACKGROUND

The present invention relates to novel compounds of use in treatment of methicillin resistant *Staphylococcus aureus* (MRSA) infection in conjunction with β-lactam antibiotics.

*S. aureus* is one of the major causes of both nosocomial and community-acquired infections worldwide. The use and overuse of β-lactam agents and other antibiotics has resulted in intense selective pressure on bacterial populations and led to the emergence of multi-drug resistant bacteria that threaten our ability to treat serious infections, particularly in hospitals. Over the last 15 years there has been a steady rise in the incidence of methicillin-resistant *S. aureus* (MRSA) and the latest figures from the PHLS Communicable Disease Surveillance Centre indicate that, in England and Wales, about 45% of *S. aureus* isolates are now resistant to this agent. Staphylococci show a strong tendency to accumulate antibiotic resistant genes and the majority of MRSA isolates are now resistant to a range of antibiotics. Ominously, MRSA strains carrying the enterococcal vanA gene complex and expressing high-level resistance to vancomycin have recently been identified in clinical specimens from two unrelated cases. The introduction of Synercid and Linezolid and the anticipation of a third agent with activity against MRSA (Daptomycin) supplements the anti-MRSA armamentarium but there remains an urgent need for new treatments for these infections, in particular agents that suppress or abrogate the emergence of resistance. We are examining the therapeutic potential of agents that do not directly kill the target bacterial population but modify them to produce a "less fit" phenotype with reduced capacity to survive at the site of infection. There are conceptual reasons to suppose that this approach will result in less selective pressure on the bacteria and delay the emergence of resistant genotypes.

Polyphenolic components extracted from Japanese green tea (*Camellia sinensis*) possessed a number of activities against methicillin resistant *S. aureus* (MRSA) (Yam, T. S. et al 1997; Yam, T. S. et al 1998; Stapleton, P. D. et al (2002)) in addition to weak direct antibacterial activity, extracts were able to suppress the activity of staphylococcal β-lactamases. In addition, at subinhibitory concentrations they were also able to sensitise MRSA strains to methicillin and other semi-synthetic β-lactam antibiotics; this effect was marked and reduced the Minimum Inhibitory Concentration (MIC) of test strains from full resistance to below the antibiotic break point.

Initial observations were made using aqueous extracts of green tea; partition chromatography was then used to fractionate the material (Yam, T. S. et al. 1997). Activity was confined to one fraction that was enriched for the compound epigallocatechin gallate ECg, an abundant polyphenolic component of green tea, but other constituents were present in small amounts.

Unfortunately, epicatechin gallate cannot be widely administered because it is broken down by esterases in the body to the inactive products, epicatechin and gallic acid (Kohri, T. et al, 2001).

It has been observed that MRSA grown in the presence of sub-inhibitory concentrations of tea extracts have thickened cell walls and form pseudomulticellular aggregates (Hamilton-Miller, J. M. T et al (1999)). Green tea administered as a spray has been successfully used in the treatment of an MRSA infection of the trachea (windpipe) (Yamashita, S. et al (2001)).

Stapleton et al. (2004) describe some investigations into the molecular mechanism of β-lactam sensitisation to establish a basis for the rational selection of pharmacologically acceptable molecules, investigated structure-activity relationships (SAR) to identify pharmacophores within active molecules. The capacity of catechins and gallates to modulate β-lactam resistance was evaluated by testing the compound at a fixed concentration in combination with oxacillin. Modulating activity was defined as a greater than two-fold reduction in the MIC of a β-lactam when tested in combination with a fixed sub-inhibitory concentration of the test compound. ECg converted MRSA strain BB568, which has a MIC of 256 mg/L for oxacillin, to the fully drug sensitive phenotype (1 mg/L) and below the breakpoint. EGCg reduced the MIC of BB568 to 8 mg/L; epicatechin (EC) and epigallocatechin (EGC), the two most abundant non-gallyl catechins in tea, were inactive in the combination assay. These compounds were tested against a comprehensive collection of 40 MRSA strains isolated from a variety of countries; epidemic MRSA strains from the UK were included. With all strains, ECg reduced the MIC values to the susceptibility breakpoint or below.

The physical properties of ECg and EGCg suggest these molecules have the capacity to intercalate into target membrane bilayers and perturb the function of key membrane-associated proteins in peptidoglycan synthesis, such as femA, femB and mecA gene products; it is highly likely that such an interaction would also reduce or prevent the transport of proteins not essential for cell viability across the bilayer. Japanese workers have shown that catechins are able to bind to artificial lipid bilayers (Nakayama, T. et al 1998, Hashimoto, T. et al 1999) and recent work (Kajiya, K. et al 2001 and Kajiya, K. et al 2002) shows that binding affinities appear to correlate with the bioactivity of catechins in our assay. Thus, ECg has a greater propensity to intercalate into the phospholipid palisade than EGCg, catechin or EC (Cartula, N. et al 2003). Binding has been shown to be dependent upon the number of hydroxyl groups on the B-ring catechins with two hydroxyl groups, such as ECg, have a greater membrane binding capacity than those with three hydroxyl groups, such as EGCg (Kajiya, K. et al 2001). The binding of ECg to liposomes is enhanced in the presence of EC (Kajiya, K. et al 2002).

Surprisingly, it has been found that intercalation of catechin gallates into the cytoplasmic membrane interferes with the export of proteins such as—toxin and coagulase and raises the possibility that the compounds may reduce the virulence of Gram-positive bacteria such as *S. aureus* at the site of infection and thus significantly contribute to their removal from the body by immune processes (Taylor, P. et al. 2004).

SUMMARY

According to the invention there is provided a new compound of the general formula I

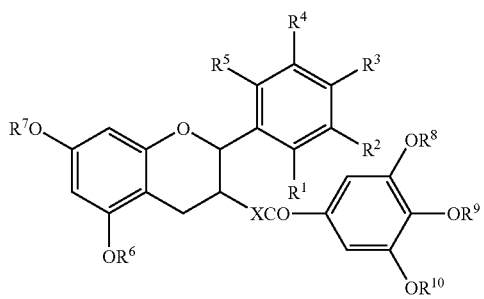

in which $R^8$ to $R^{10}$ are individually selected from the group consisting of hydrogen, aryl, $C_{1-6}$ alkyl, trialkylsilyl and acyl; $R^1$ to $R^5$ are individually selected from the group consisting of hydrogen, hydroxy, $C_{1-6}$ alkoxy and acyloxy; $R^6$ and $R^7$ are each selected from the group consisting of H, $C_{1-4}$ alkyl, trialkylsilyl and acyl;

X is O or NR, and R is H or Me; in which any of the alkyl groups including alkyl groups in alkoxy, acyl and acyloxy groups may be substituted by one or more aryl, $C_{1-4}$ alkyl, $C_{1-4}$ alkoxy, hydroxyl, trialkylsilyoxy or acyloxy groups; with the proviso that $R^2$ and $R^3$ are not both OH when $R^4$ is H or OH, $R^1$ and $R^5$ are both H, and X is O.

DETAILED DESCRIPTION OF EMBODIMENTS

Preferably, each of $R^1$ to $R^5$ is selected from hydrogen or hydroxy. Most preferably, one or two of $R^1$ to $R^5$ is/are hydroxy. When only one of $R^1$ to $R^5$ is hydroxy, this is preferably $R^2$ or $R^3$ and the remainder of $R^1$ to $R^5$ are H. A preferred compound wherein $R^2$ is OH, has H or OH as $R^4$ and H as $R^1$, $R^3$ and $R^5$. In a further preferred embodiment, four of $R^1$ to $R^5$ are OH.

Compounds of the present invention may be esters (that is, wherein X is O) or amides (wherein X is NR).

With regard to the stereo chemistry of the compounds, it is preferred that the compound be in one of the forms Ia or Ib

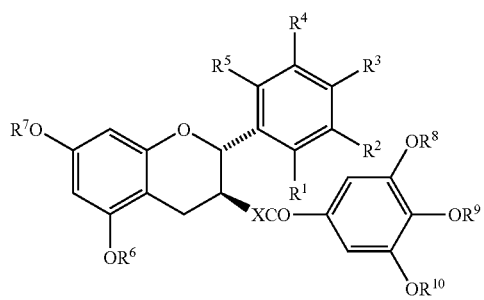

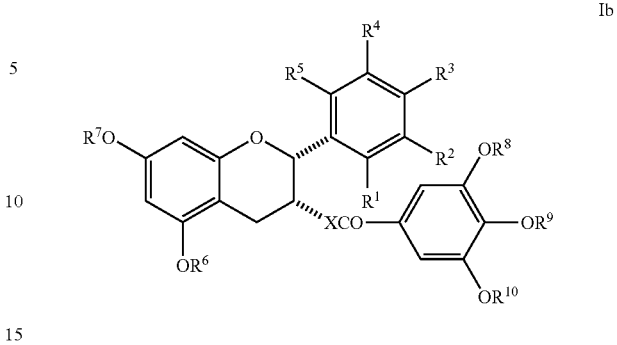

The stereoisomers with structure Ib are believed to have optimal activity.

Compounds of the general formula I wherein X is NR and $R^2$ and $R^3$ are hydroxy and each group $R^4$, $R^6$ and $R^7$ are hydrogen, are analogues of the naturally occurring compound ECg, wherein the ester linkage is replaced by an amide linkage. Compounds of this definition wherein $R^4$ is not H, but OH, are analogues of the naturally occuring compound EGCg. Such compounds have similar activity to the corresponding ester and are less susceptible of esterase hydrolysis.

In general formula I, wherein X is NR, in the B ring (the upper ring), the substituents $R^1$ to $R^5$ preferably include at least one group other than hydrogen para to the attachment to the C ring. The other group is preferably ortho to this group. Where there are three substituents other than hydrogen, the substituents are preferably para and meta to the attachment. Preferably such substituents are hydroxyl or, for precursor compounds, protected hydroxyl. Compounds in which there are 2 substituents other than hydrogen are believed to have better membrane binding properties than those which have 3.

In the embodiment wherein X is NR, R is preferably H. $R^2$ and $R^3$ are preferably not both OH when $R^1$, $R^4$ and $R^5$ are H.

The pharmacological profile of naturally occuring compound ECg may be improved by varying the degree of hydroxylation of the B-ring. Since ECg differs from EGCg only by the absence of a hydroxyl function, and ECg has a greater affinity for membrane bilayers than EGCg, it is believed that further reduction in the degree of hydroxylation of the B-ring will enhance anti-MRSA effects by increasing the affinity of these analogues for lipid bilayers.

The following ester compounds are believed to have greater activity than the natural compounds:

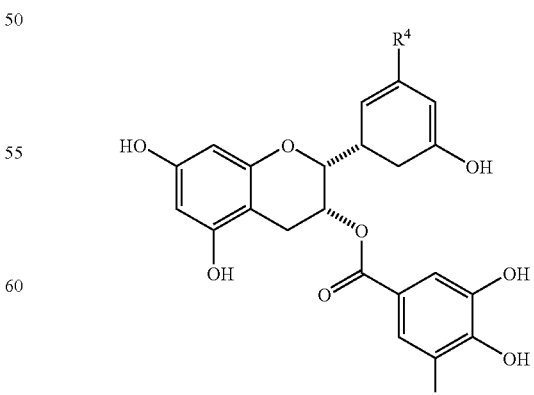

$R^4$ = H or OH

-continued

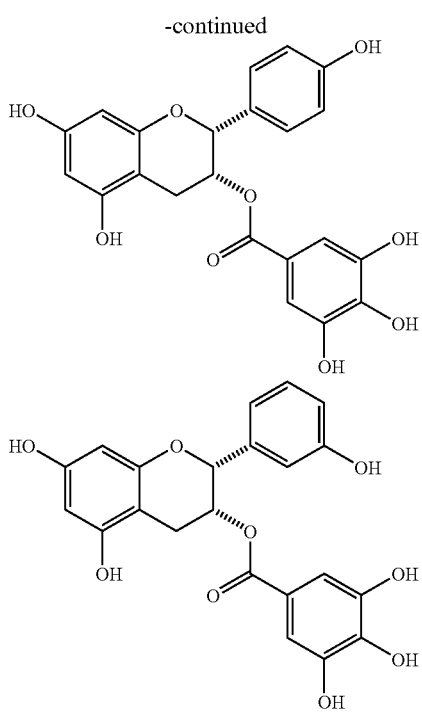

Those compounds that do not possess the para-hydroxyl group in the B ring may also be less prone to epimerisation via a quinine methine-like intermediate due to removal of this anchimeric substituent.

Preferably each of $R^8$, $R^9$ and $R^{10}$ are H. In a further preferred embodiment, $R^6$ and $R^7$ are H.

Compounds in which any of the groups $R^6$ to $R^{10}$ represent other than hydrogen may be precursors for the active compounds. It is possible that these precursors may be incorporated into compositions for administration, provided they are capable of being metabolised in the body to form the active compounds. Preferably, however, the precursors are reacted, to generate hydroxyl groups from the protected hydroxyl groups represented by $OR^x$ where $R^x$ is one or more of $R^6$ to $R^{10}$.

Protecting groups $R^6$, $R^7$, $R^8$, $R^9$ and $R^{10}$ may be the same as or different from one another. Usually $R^6$ is the same as $R^7$ and all groups $R^8$ to $R^{10}$ are the same as one another. Preferably the groups $R^6$ and $R^7$ are the same as the groups $R^8$ to $R^{10}$. Usually the protecting groups are reacted onto the hydroxyl groups of a compound already comprising the two rings (the B and D rings) in its skeleton. Consequently the same protecting groups will be generated. By having the same protecting groups, whether or not derived by reacting a compound having a skeleton including both rings, or by conjugating together compounds having one or the other ring, deprotection can take place in a convenient and simple step involving a single deprotection step. Where the groups $R^6$ and $R^7$ and groups $R^8$ to $R^{10}$ are the same, the same deprotection step will remove all protecting groups. Of course a person skilled in the art would be able to devise sequential deprotection steps with different reagents where the groups are different.

Suitable hydroxyl protecting groups are tertiary butyldimethylsilyl (TBS), acyl, alkyl or aralkyl, such as benzyl or tertiary butyl.

The present invention provides novel compositions comprising the novel ester and amide compounds as described above, and a carrier, for instance pharmaceutical compositions which comprise a pharmaceutically acceptable excipient. The invention also provides a method of treatment of methicillin resistant *S. aureus* infection in which the novel compound is administered to an human or animal. Usually the compound is administered in conjunction with a β-lactam antibiotic to treat a *S. aureus* infection. Compositions may, conveniently, contain both the novel compound and the antibiotic.

The compounds are believed to have activity in reducing the β-lactam resistance of infections when co-administered at a level to give local concentrations of around 0.5 to 10 mg/l. The compounds may be administrable orally but preferably are administered systemically, preferably parenterally, or locally, for instance topically. The compositions are thus adapted for the appropriate mode of administration. A suitable daily dosage for an adult human patient may be in the range 50 to 1000 mg/day. It may be necessary to administer the daily dosage in several dosage units, for instance at intermittent periods during the day.

According to the present invention there is also provided a method for synthesising the novel compounds. In the new method a compound of the formula II

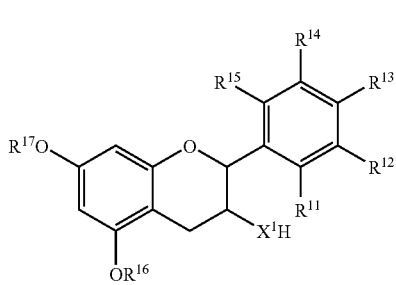

II in which $X^1$ is O or $NR^{21}$; $R^{11}$-$R^{15}$ are either H or $OR^{22}$; $R^{21}$ is H or Me; the or each $R^{22}$ is a hydroxyl protecting group; and $R^{16}$ and $R^{17}$ are each a hydroxyl protecting group, is reacted with an acylating compound of the formula III

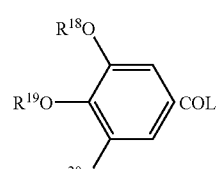

III in which each of $R^{18}$, $R^{19}$ and $R^{20}$ is a hydroxyl protecting group and L is a leaving group to produce a compound of the formula IV

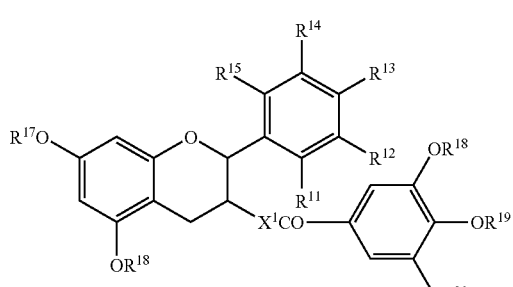

IV in which $X^1$ and $R^{11}$-$R^{20}$ and $R^{15}$ have the same meanings as in the starting compounds.

Where X in the compound of formula II is $NR^{21}$ and the desired final product has a methyl substituent as a group R, this may be added by a derivatisation reaction carried out after formation of the amide bond, by reaction of a compound of the formula IV in which $R^{21}$ is hydrogen with a methylating reagent such as methyl halide.

The method of the invention may include deprotection steps following the formation of the ester or amide bond, in which one or more groups $R^{16}$-$R^{20}$ representing hydroxyl protecting groups are removed and replaced by hydrogen. If any of $R^{11}$-$R^{15}$ represent protected hydroxyl groups, these too may be deprotected.

The starting amine is also a new compound. According to a further aspect of the invention such novel compounds are defined by formula X

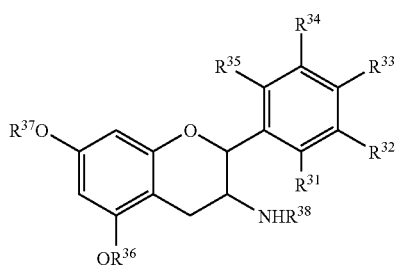

in which
  each of $R^{31}$-$R^{35}$ is hydrogen or a protected hydroxyl group;
  each of $R^{36}$ and $R^{37}$ is hydrogen or a hydroxyl protecting group;
  and $R^{38}$ is hydrogen, methyl or an amine protecting group.

In compounds of the formula X, a protected hydroxyl is a group $OR^y$ where $R^y$ is the hydroxyl protecting group. In the compounds the hydroxyl protecting groups may be any of those defined above with reference to compounds of the formula I. The amine protecting groups may be any of those conventionally used in synthetic peptide chemistry, for instance benzyloxycarbonyl, butyloxycarbonyl, fluorenyl-9-methoxy-carbonyl, 2-[biphenylyl-(4)]-propyl-2-oxycarbonyl-, dinitrophenyl, tosyl, alkyl or benzyl. Preferably $R^{38}$ is benzyl.

The amine compound, either the starting material of the formula II wherein $X^1$ is $NR^{21}$ or the novel compound of the formula X, may be made in a preliminary step by reductive amination of a compound of the formula V

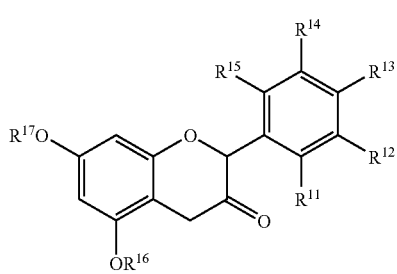

in which the groups $R^{11}$ to $R^{17}$ have the same meanings as in the compound II with an amine reagent of general formula VI $$H_2NR^{23} \qquad\qquad VI$$

in which $R^{23}$ is hydrogen, an alkyl group or an aralkyl group, and a reducing agent to produce a compound of formula VII

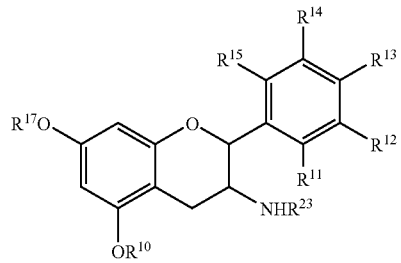

in which $R^{11}$ to $R^{17}$ and $R^{23}$ have the same meanings as in the respective starting compounds.

In this method, $R^{23}$ in the compound of formula VII produced in the reaction with amine reagent and reducing agent may be different to $R^{21}$ in the amine compound which is reacted with the acylating compound. In this case, the method includes the step of replacing the group $R^{23}$ of the compound of formula VII by a group $R^{21}$ which is a hydrogen atom or a methyl group prior to reaction with the acylating compound. Preferably, $R^{23}$ is benzyl.

The method may also include a preliminary step in which the compound of formula V is produced by oxidation of an alcohol compound of the formula VIII

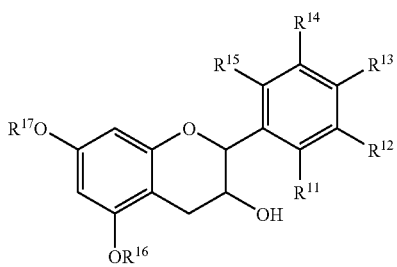

in which $R^{11}$ to $R^{17}$ have the same meanings as in the compound of formula V, using an oxidising agent. Preferably, the oxidising agent is Dess-Martin periodinane.

Some ketone compounds of the formula V may be novel compounds. According to a further aspect of the invention, there are claimed novel compounds compound of formula IX

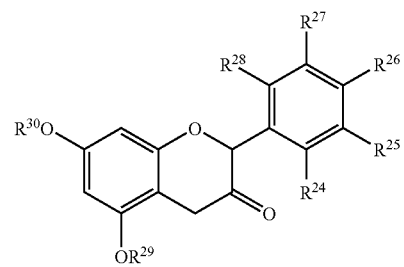

in which $R^{29}$ and $R^{30}$ are H or hydroxyl protecting groups and each $R^{24}$-$R^{28}$ is H or a protected hydroxyl group.

The ketone compound of the formula IX may be produced by a method of oxidation of an alcohol compound of the formula XI

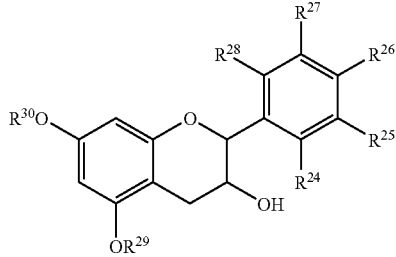

XI in which each of $R^{24}$-$R^{28}$ is H, hydroxyl or a protected hydroxyl group; and $R^{29}$ and $R^{30}$ are each hydrogen or a hydroxyl protecting group.

The alcohol starting compound of the formula XI or VIII, as the case may be, may either be produced by wholly synthetic methods or, preferably, may be produced by hydrolysis of a naturally occurring EGCg or ECg compound as the case may be.

Compounds of formula XI in which each of $R^{24}$-$R^{28}$ are H, hydroxyl or a protected hydroxyl and $R^{29}$ and $R^{30}$ are each hydrogen or a hydroxyl protecting group may also be novel compounds. Accordingly, the present invention provides compounds of formula XIII

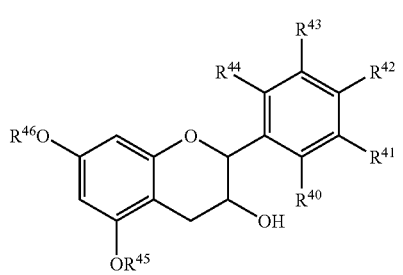

XIII in which each of $R^{40}$-$R^{44}$ is H, hydroxyl or a protected hydroxyl group; and $R^{45}$ and $R^{46}$ are each hydrogen or a hydroxyl protecting group.

The invention also provides a method of synthesising a compound of formula XIII including the preliminary steps of reacting the alkene of formula XIV

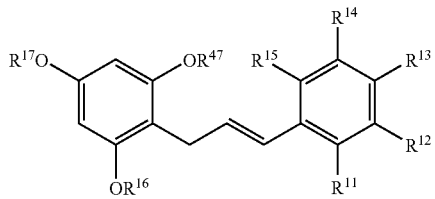

XIV wherein each of $R^{11}$-$R^{15}$ is H, hydroxyl or a protected hydroxyl, and $R^{16}$ and $R^{17}$ are each hydrogen or a hydroxyl protecting group and $R^{47}$ is a hydroxyl protecting group;

with a dihydroxylation reagent to give the corresponding diol of formula XV

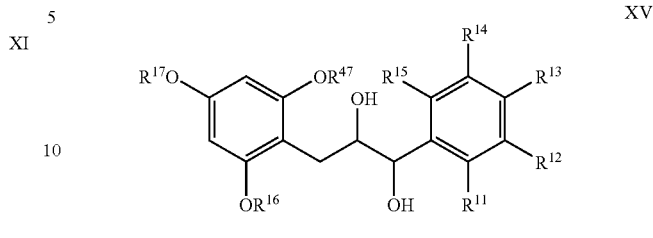

XV followed by reaction with an acetyl halide and ring closure to give the compound of formula XIII.

Preferably the halide is bromide. A suitable hydroxylation reagent is AD-mix-β, although other suitable reagents may be used.

In this method, the alkene compound of formula XIV may be synthesised by reaction of starting aldehyde XVI with starting ketone of formula XVII

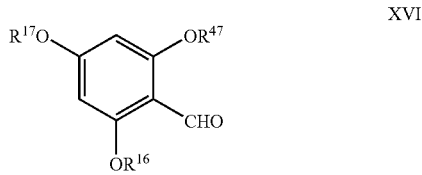

XVI

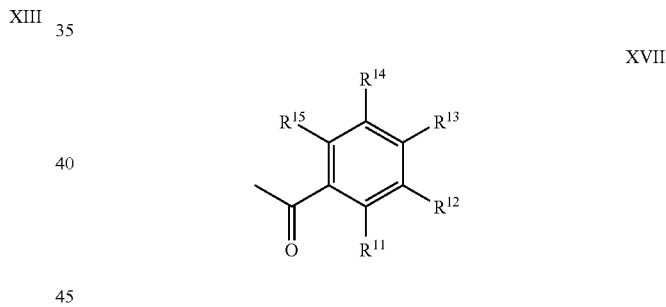

XVII in which the groups of $R^{11}$-$R^{17}$ and $R^{47}$ have the same meanings as in the desired product XIV to give the adduct of the formula XVIII

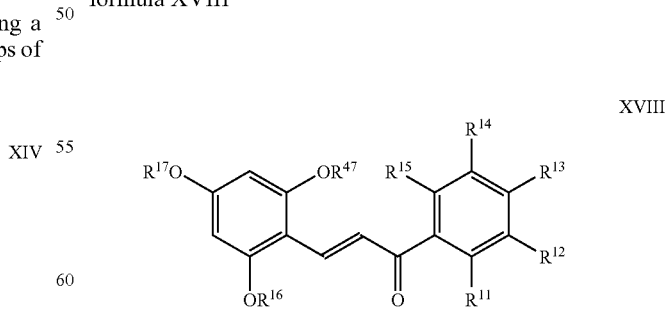

XVIII in which $R^{11}$-$R^{17}$ and $R^{47}$ are the same as in the starting compounds XVI and XVII followed by reduction and elimination to give the compound XIV.

The following compounds are also novel:

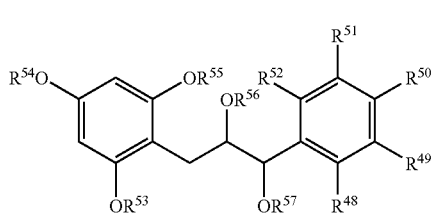 XIX

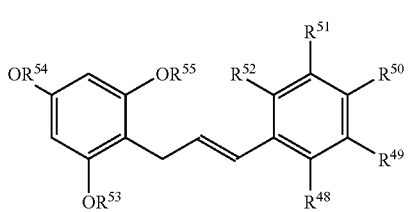 XX

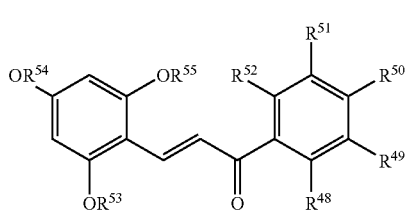 XXI wherein each of $R^{48}$-$R^{52}$ is H, hydroxyl or a protected hydroxyl and $R^{53}$-$R^{55}$ and $R^{56}$-$R^{57}$ (if present) are each hydroxyl or a hydroxyl protecting group.

In worked examples 1-7 below we show that an amide is more hydrolytically stable than the analogous ester. The examples illustrate the invention and support our hypothesis concerning the activity of the amide compounds. Example 8 describes the synthesis of two B-ring modified (−)-epicatechin gallate analogues. Example 9 illustrates the efficacy of the compounds synthesised in example 8 as modulators for β-lactam resistance in S. aureus.

Example 1

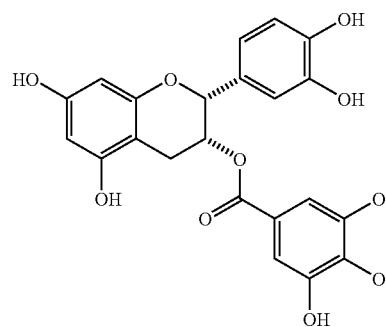

1

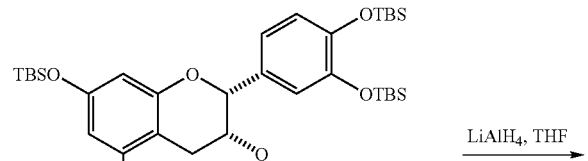

2

3

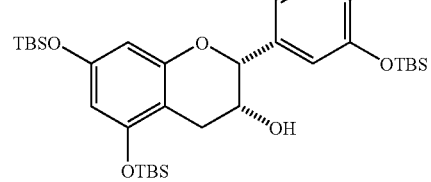

4

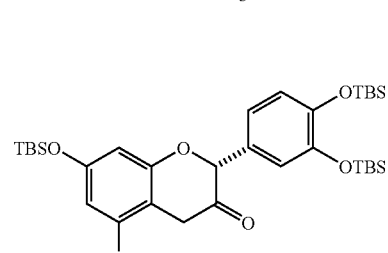

5

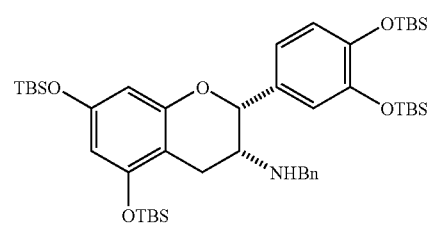

6

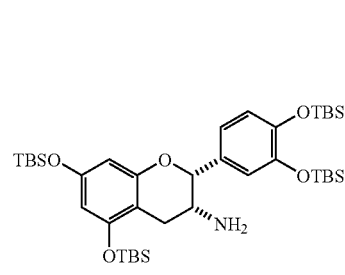

7

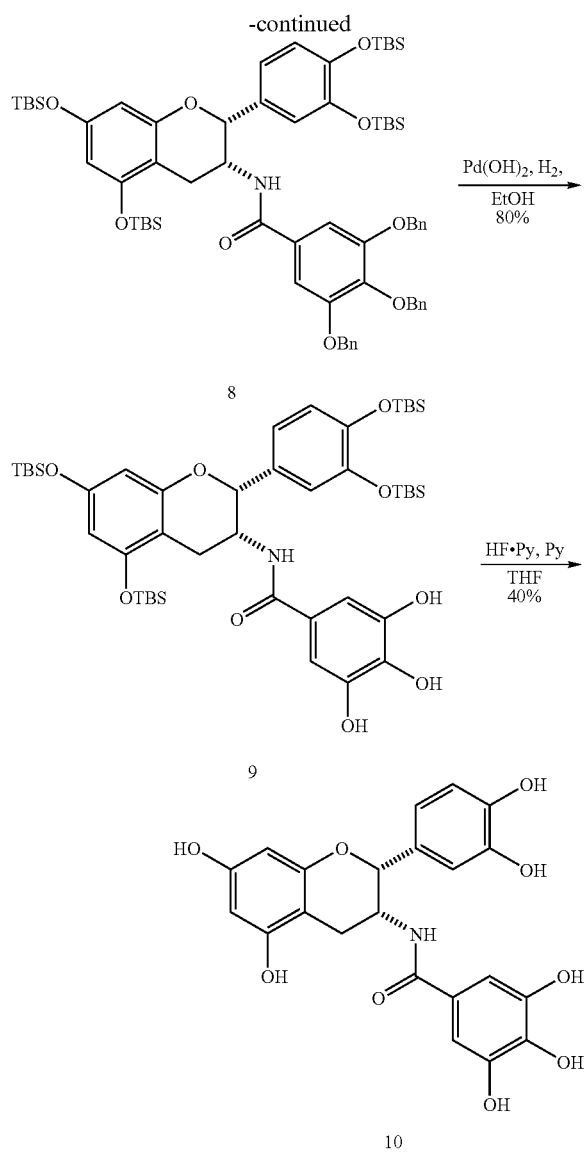

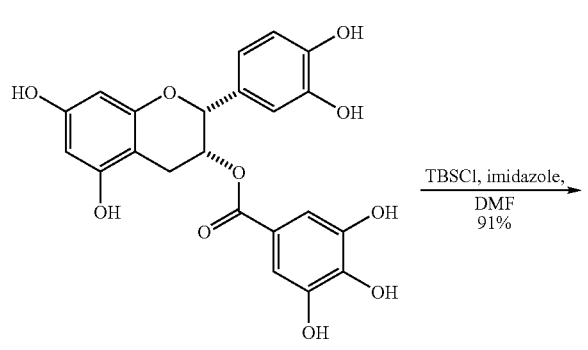

Example 1A (−)-ECG-7TBS

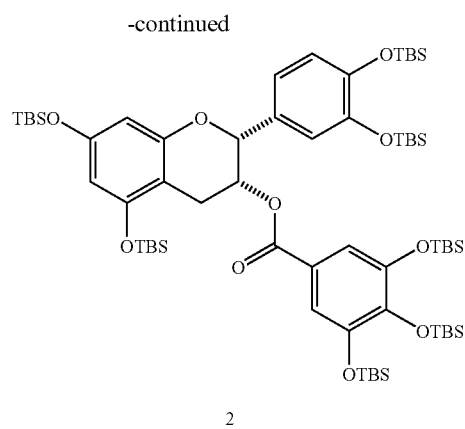

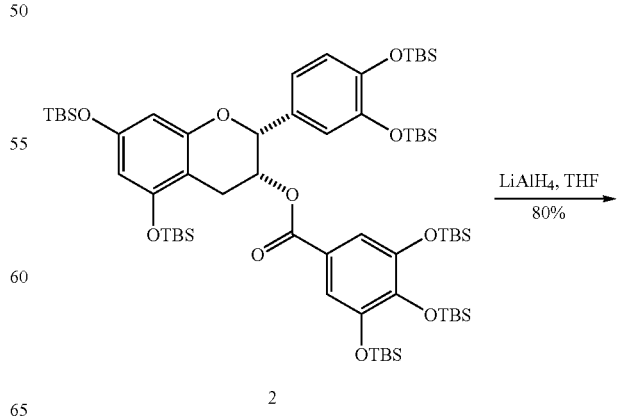

To a solution of (−)-epicatechin gallate 1 (2.0 g, 4.4 mmol), in DMF (10 mL) at 0° C. was added imidazole (3.0 g, 0.044 mol) followed by tert-butyldimethylsilyl chloride (6.6 g, 0.044 mol) and the mixture was allowed to warm to room temperature overnight. On completion of reaction the mixture was diluted with water (20 mL). The product was then partitioned between ether (2×20 mL) and water (20 mL). The organics were then combined, dried with MgSO$_4$, filtered and concentrated in vacuo to yield a colorless oil which was purified by flash chromatography (eluting with 5% Et$_2$O: Pet Ether) to give the product 2 as a colorless oil, 5.0 g, 91%; δ$_H$ (400 MHz, CDCl$_3$) 0.08-0.21 (m, 42H, 7×OSi(CH$_3$)$_2$C(CH$_3$)$_3$), 0.90-0.98 (m, 63H, 7×OSi(CH$_3$)$_2$C(CH$_3$)$_3$), 2.97 (d, 2H, J 3.1, ArCH$_2$CHCHO), 5.05 (s, 1H, ArCH$_2$CHCHO), 5.56 (m, 1H, ArCH$_2$CHCHO), 5.96 (d, 1H, J 2.3, ArH), 6.18 (d, 1H, J 2.3, ArH), 6.74 (d, 1H, J 8.7, ArH), 6.89 (d, 1H, J 2.1, ArH) 6.95 (dd, 1H, J 8.3, 2.1, ArH), 7.09 (s, 2H, 2×ArH); δ$_C$ (100 MHz, CDCl$_3$) −4.4, −4.3, −4.2 −4.1, −3.9, −3.7, 18.1, 18.2, 18.3, 18.4, 18.8, 25.7, 25.8, 25.9, 26.1, 26.7, 68.0, 76.7, 101.7, 103.7, 103.9, 115.3, 119.3, 119.7, 120.8, 121.7, 131.1, 142.9, 146.6, 148.2, 154.7, 154.9, 155.6, 165.0; MS (m/z). No mass ion observed; [α]$_D$ −57.9° (c 1.0, CHCl$_3$, at 25° C.).

Example 1B

EC-4TBS-OH

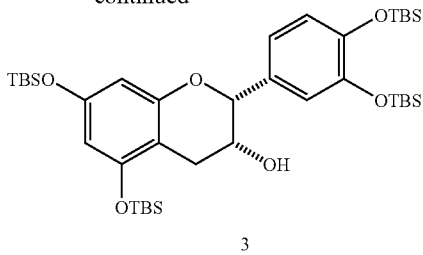

3

To a solution of (−)-ECG-7TBS 2 (5 g, 4.0 mmol), in THF (200 mL) at 0° C. was added a solution of lithium aluminium hydride in THF (1M, 4.0 mL) and the mixture was monitored by TLC. After 30 minutes the mixture was diluted with water (0.4 mL) followed by the addition of 15% NaOH aq (0.4 mL) followed by water (1.0 mL) and the resulting precipitate was filtered through celite. The crude product was purified by flash chromatography (eluting with 5% Et$_2$O: Pet Ether) to give the product 3 as a colorless oil, 2.4 g, 80%; $v_{max}$/cm$^{-1}$ 2930; $\delta_H$ (400 MHz, CDCl$_3$) 0.20-0.24 (m, 24H, 4×OSi(CH$_3$)$_2$C(CH$_3$)$_3$), 0.98 (s, 9H, OSi(CH$_3$)$_2$C(CH$_3$)$_3$), 0.99 (s, 9H, OSi(CH$_3$)$_2$C(CH$_3$)$_3$), 1.00 (s, 9H, OSi(CH$_3$)$_2$C(CH$_3$)$_3$), 1.02 (s, 9H, OSi(CH$_3$)$_2$C(CH$_3$)$_3$), 1.72 (d, 2H, J 6.2, ArCH$_2$CHCHO), 2.89 (brd, 1H, J 3.5, OH 4.22-4.24 (m, 1H, ArCH$_2$CHCHO), 4.90 (s, 1H, ArCH$_2$CHCHO), 5.99 (d, 1H, J 2.3, ArH), 6.14 (d, 1H, J 2.3, ArH), 6.86-6.88 (m, 2H, 2×ArH), 6.94 (d, 1H, J 2.0, ArH) 6.97-6.98 (m, 2H, 2×ArH); $\delta_C$ (125 MHz, CDCl$_3$) −4.3, −4.0, −3.8, −3.7, 18.2, 18.3, 18.5, 18.8, 25.7, 25.8, 26.0, 26.3, 28.7, 66.1, 78.1, 101.6, 104.1, 119.4, 121.1, 131.3, 146.8, 147.0, 155.0, 155.1, 155.5; MS (FAB, m/z) 747 (M+1, 100%), 729 (M−17, 55%); HRMS (FAB, m/z) found M 746.4221, C$_{39}$H$_{70}$O$_6$Si$_4$ requires M 746.4250; [α]$_D$ −7.3° (c 1.0, CHCl$_3$, at 25° C.).

Example 1C

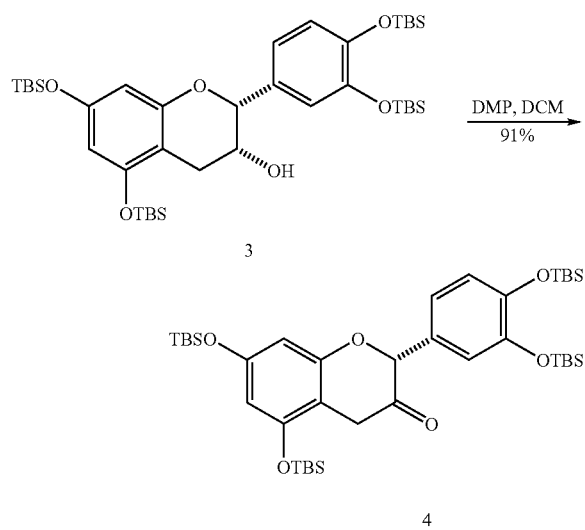

To a solution of alcohol 3 (1.0 g, 1.3 mmol), in DCM (10 mL) at 0° C. was added Dess-Martin periodinane (620 mg, 1.4 mmol) and the mixture was monitored by TLC. After 9 hours the mixture partitioned between 1M NaOH aq (10 mL) and DCM (2×10 mL). The organics were then combined, washed with brine (20 mL), dried with MgSO$_4$, filtered and concentrated in vacuo. The crude product was purified by flash chromatography (eluting with 5% Et$_2$O: Pet Ether) to give the product 4 as a colorless oil, 870 mg, 91%; $v_{max}$/cm$^{-1}$ 2928, 1508; $\delta_H$ (400 MHz, CDCl$_3$) 0.15-0.25 (m, 24H, 4×OSi(CH$_3$)$_2$C(CH$_3$)$_3$), 0.96-1.03 (m, 36H, 4×OSi(CH$_3$)$_2$C(CH$_3$)$_3$), 3.50 (d, 2H, J 2.3, ArCH$_2$CHCHO), 5.26 (s, 1H, ArCH$_2$CHCHO), 6.07 (d, 1H, J 2.2, ArH), 6.28 (d, 1H, J 2.2, ArH), 6.81-6.82 (m, 3H, 3×ArH); $\delta_C$ (125 MHz, CDCl$_3$) −4.0, −3.9, −3.8, −3.7, 18.6, 18.8, 26.0, 26.1, 26.3, 34.6, 83.3, 103.3, 105.3, 105.6, 119.8, 120.2, 121.4, 128.7, 147.4, 147.5, 154.4, 154.9, 156.2, 205.8; MS (FAB, m/z) 744 (M+1, 100%), 368 (M−376, 98%); HRMS (FAB, m/z) found M 744.4127, C$_{39}$H$_{68}$O$_6$Si$_4$ requires M 744.4093; [α]$_D$ +24.0° (c 1.2, CH$_2$Cl$_2$, at 24° C.).

Example 1D

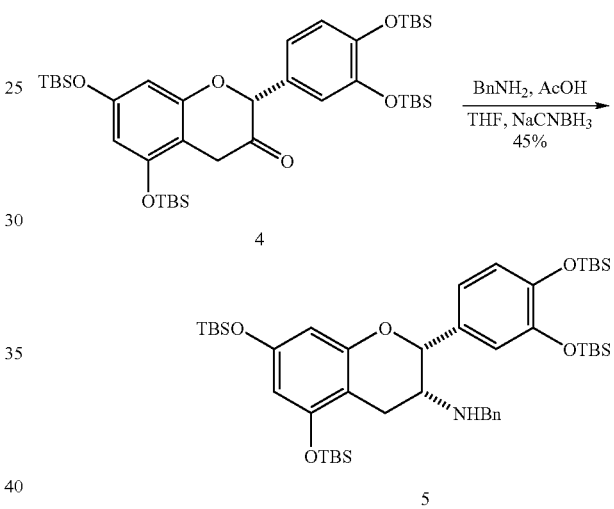

To a solution of ketone 4 (500 mg, 0.67 mmol), in THF (10 mL) was added benzylamine (0.15 mL, 1.3 mmol) followed by acetic acid (3 drops) and the mixture was stirred for 30 minutes before the addition of sodium cyanoborohydride in THF (1M, 0.74 mL). The mixture was then stirred at room temperature overnight. The product was partitioned between ether (2×20 mL) and water (20 mL). The organics were then combined, dried with MgSO$_4$, filtered and concentrated in vacuo to yield a yellow oil which was purified by flash chromatography (eluting with 10% Et$_2$O: Pet Ether) to give the product 5 as a colorless oil, 250 mg, 45%; $v_{max}$/cm$^{-1}$ 2955, 2930, 2858; $\delta_H$ (400 MHz, CDCl$_3$) 0.16-0.27 (m, 24H, 4×OSi(CH$_3$)$_2$C(CH$_3$)$_3$), 0.99-1.29 (m, 36H, 4×OSi(CH$_3$)$_2$C(CH$_3$)$_3$), 2.70 (dd, 1H, J 17, 4.8, ArCH$_2$CHCHO), 2.78 (dd, 1H, J 17, 4.8, ArCH$_2$CHCHO), 3.21-3.23 (m, 1H, ArCH$_2$CHCHO), 3.71 (d, 1H, J 14, NCH$_2$Ar), 3.83 (d, 1H, J 14, NCH$_2$Ar), 5.09 (d, 1H, J 2.2, ArCH$_2$CHCHO), 5.99 (d, 1H, J 2.3, ArH), 6.14 (d, 1H, J 2.3, ArH), 6.84-6.93 (m, 3H, 3×ArH), 7.12-7.28 (m, 5H, 5×ArH); $\delta_C$ (125 MHz, CDCl$_3$) −3.9, −3.8, −3.7, −3.6, 18.6, 18.7, 18.9, 25.3, 26.2, 26.3, 26.4, 51.4, 53.1, 78.7, 101.8, 104.0, 105.6, 119.6, 119.7, 121.2, 127.1, 128.3, 128.6, 132.5, 146.6, 147.1, 155.2, 156.1; MS (FAB, m/z) 836 (M+1, 75%), 484 (M−351, 100%); HRMS (FAB, m/z) found M 836.4991, $C_{46}H_{78}NO_5Si_4$ requires M 836.4957; $[\alpha]_D$ −3.3° (c 1.0, $CH_2Cl_2$, at 23° C.).

Example 1E

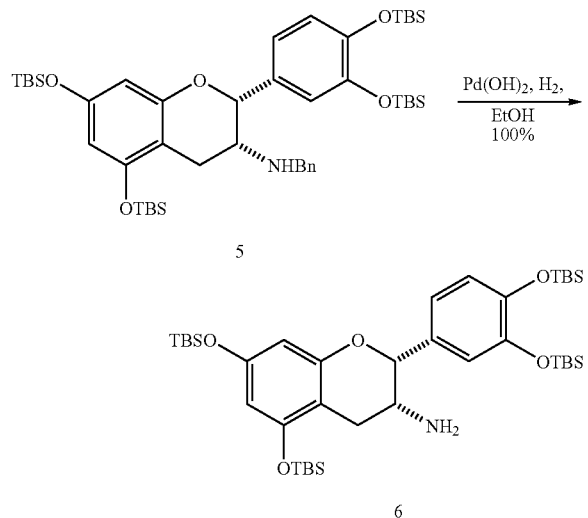

To a solution of amine 5 (420 mg, 0.51 mmol), in EtOH (10 mL) and 5% palladium on activated carbon (10 mg) and the mixture was stirred vigorously under an atmosphere of hydrogen for 16 hours. The product was filtered through celite and concentrated in vacuo to yield a brown oil which was purified by flash chromatography (eluting with 20% $Et_2O$: Pet Ether) to give the product 6 as a colorless oil, 380 mg, 100%; $\nu_{max}/cm^{-1}$ 2956, 2929, 2858; $\delta_H$ (400 MHz, $CDCl_3$) 0.10-0.39 (m, 24H, $4\times OSi(CH_3)_2C(CH_3)_3$), 1.02-1.10 (s, 36H, $4\times OSi(CH_3)_2C(CH_3)_3$), 2.57-2.63 (m, 2H, $ArCH_2CHCHO$ and $NH_2$), 2.76-2.80 (m, 1H, $NH_2$), 2.89 (dd, 1H, J 16, 5.0, $ArCH_2CHCHO$), 3.29-3.31 (m, 1H, $ArCH_2CHCHO$), 5.17 (d, 1H, J 2.7, $ArCH_2CHCHO$), 6.06 (d, 1H, J 2.3, ArH), 6.19 (d, 1H, J 2.2, ArH), 6.88-6.97 (m, 3H, 3×ArH); $\delta_C$ (125 MHz, $CDCl_3$) −4.0, −3.8, −3.7, 1.4, 18.6, 18.7, 18.8, 26.1, 26.2, 26.3, 26.4, 42.1, 54.3, 78.5, 101.8, 103.9, 105.9, 119.5, 119.8, 121.1, 132.3, 146.6, 147.1, 155.1, 155.2 156.1; MS (FAB, m/z) 746 (M+1, 15%), 644 (M−101, 15%); HRMS (FAB, m/z) found M 746.4450, $C_{39}H_{72}NO_5Si_4$ requires M 746.4409; $[\alpha]_D$ −4.6° (c 4.0, $CH_2Cl_2$, at 25° C.).

Example 1F

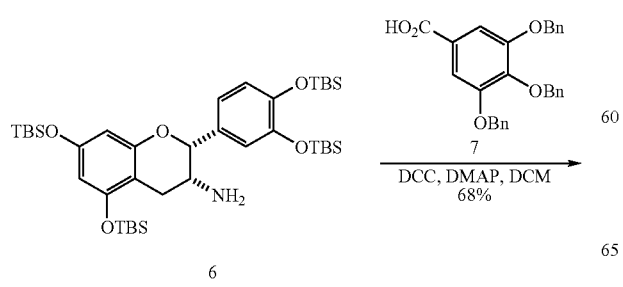

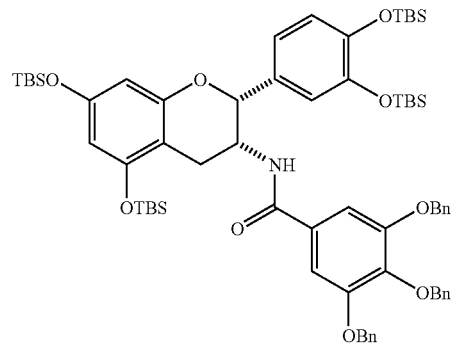

To a solution of protected gallic acid 7 (130 mg, 0.29 mmol), in DCM (5.0 mL) was added DCC (64 mg, 0.31 mmol) and DMAP (5 mg) and the mixture was stirred for 20 minutes. Amine 6 (190 mg, 0.26 mmol) was then added in DCM (2.0 mL) and the mixture was stirred at room temperature for 16 hours. The resulting precipitate was then filtered and the filtrate concentrated in vacuo to yield a yellow oil which was purified by flash chromatography (eluting with 20% $Et_2O$: Pet Ether) to give the product 8 as a colorless oil, 210 mg, 68%; $\nu_{max}/cm^{-1}$ 2954, 1582, 1508; $\delta_H$ (500 MHz, $CDCl_3$) 0.25-0.38 (m, 24H, $4\times OSi(CH_3)_2C(CH_3)_3$), 1.04-1.13 (m, 36H, $4\times OSi(CH_3)_2C(CH_3)_3$), 3.03 (dd, 1H, J 17, 3.1, $ArCH_2CHCHO$), 3.09 (dd, 1H, J 17, 5.1, $ArCH_2CHCHO$), 4.95-4.97 (m, 1H, $ArCH_2CHCHO$), 5.16 (s, 2H, $ArOCH_2Ph$), 5.17 (s, 4H, $2\times ArOCH_2Ph$), 5.20 (s, 1H, $ArCH_2CHCHO$), 6.16 (d, 1H, J 2.3, ArH), 6.19 (d, 1H, J 8.4, NH), 6.34 (d, 1H, J 2.2, ArH), 6.93-7.02 (m, 5H, 5×ArH) 7.37-7.52 (m, 15H, 15×ArH); $\delta_C$ (125 MHz, $CDCl_3$) −4.2, −4.1, −4.0, 18.3, 18.4, 18.5, 25.8, 25.9, 26.0, 46.2, 71.3, 75.2, 101.8, 104.6, 105.0, 106.9, 118.8, 118.9, 119.2, 121.0, 127.6, 127.7, 128.0, 128.1, 128.3, 128.6, 128.7, 130.1, 131.0, 136.7, 137.5, 141.2, 146.7, 152.7, 155.2, 155.3, 155.5, 166.7; MS (EI, m/z) 1169 (M+1, 50%), 735 (M−433, 100%); HRMS (EI, m/z) found M 1168.5817, $C_{67}H_{94}NO_9Si_4$ requires M 1168.6006; $[\alpha]_D$ −12.3° (c 0.2, $CHCl_3$, at 28° C.).

Example 1G

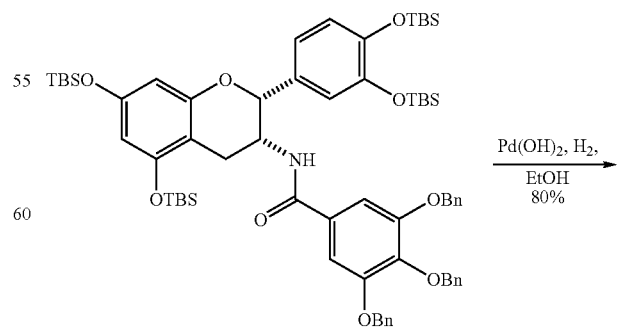

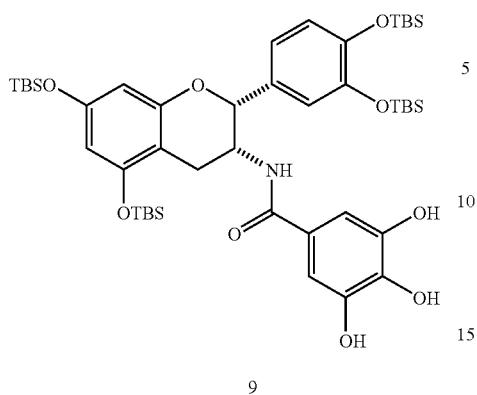

9

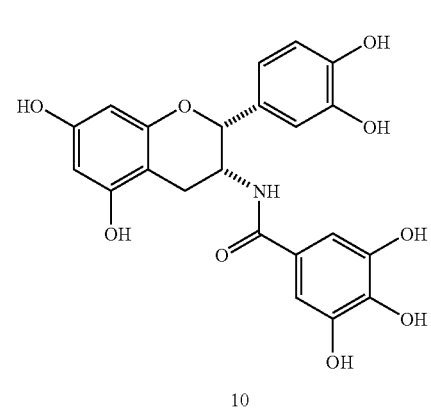

10

To a solution of amide 8 (210 mg, 0.18 mmol), in EtOH (5.0 mL) and 5% palladium on activated carbon (5.0 mg) and the mixture was stirred vigorously under an atmosphere of hydrogen for 16 hours. The product was filtered through celite and concentrated in vacuo to yield a colorless oil which was purified by flash chromatography (eluting with 30% $Et_2O$: Pet Ether) to give the product 9 as a colorless oil, 130 mg, 80%; $v_{max}/cm^{-1}$ 3339, 2930, 2858, 1613, 1514; $\delta_H$ (500 MHz, $CDCl_3$) 0.21-0.34 (m, 24H, $4 \times OSi(CH_3)_2C(CH_3)_3$), 0.99-1.11 (m, 36H, $4 \times OSi(CH_3)_2C(CH_3)_3$), 2.96 (dd, 1H, J 17, 2.5, $ArCH_2CHCHO$), 3.11 (dd, 1H, J 17, 5.5, $ArCH_2CHCHO$), 4.74-4.76 (m, 1H, $ArCH_2CHCHO$), 5.17 (s, 1H, $ArCH_2CHCHO$), 6.10 (d, 1H, J 2.2, ArH), 6.28 (d, 1H, J 2.2, ArH), 6.40 (d, 1H, J 8.7, NH), 6.76-7.17 (m, 5H, 5×ArH); $\delta_C$ (125 MHz, $CDCl_3$) −4.3, −4.2, 18.3, 18.5, 25.8, 26.0, 46.9, 65.9, 76.8, 101.8, 104.1, 104.5, 106.9, 118.6, 118.7, 121.2, 124.8, 131.0, 135.7, 144.3, 146.7, 147.1, 155.1, 155.3, 155.4 168.4; MS (EI, m/z) 898 (M+1, 80%), 454 (M−444, 100%); HRMS (EI, m/z) found M 898.4568, $C_{46}H_{76}NO_9Si_4$ requires M 898.4597; $[\alpha]_D$ −79.6° (c 2.5, $CHCl_3$, at 28° C.).

Example 1H

Amide Derivative

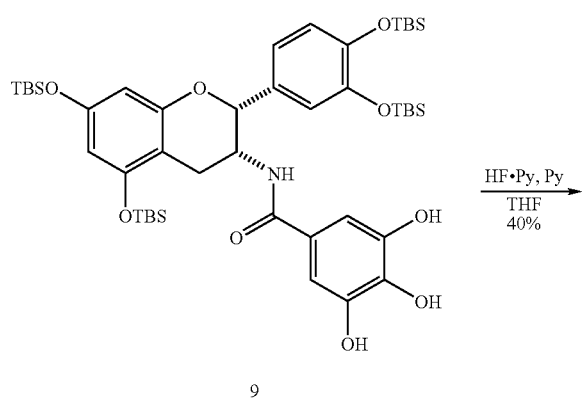

9

To a solution of amide 9 (110 mg, 0.13 mmol), in THF (2.0 mL) and pyridine (0.5 mL) and 0° C. was added HF.Py complex (0.5 mL). After 2 hours the reaction mixture was diluted with water (5 mL) and the product was extracted into EtOAc (2×10 mL). The organics were then combined, washed with saturated $CuSO_4$ (5 mL), dried with $MgSO_4$, filtered and concentrated in vacuo to yield a pale yellow solid which was purified by flash chromatography (eluting with 70% $Et_2O$: Pet Ether) to give the product 10 as a colorless oil 20 mg, 40%; $v_{max}/cm^{-1}$ 3320, 1604, 1516; $\delta_H$ (500 MHz, acetone) 2.87 (dd, 1H, J 16, 4.5, $ArCH_2CHCHO$), 3.01 (s superimposing dd, 2H, J 16, 5.2, NH and $ArCH_2CHCHO$), 4.76-4.79 (m, 1H, $ArCH_2CHCHO$), 5.27 (d, 1H, J 1.8, $ArCH_2CHCHO$), 6.06 (d, 1H, J 2.2, ArH), 6.12 (d, 1H, J 2.2, ArH), 6.82-6.93 (m, 4H, 4×ArH), 7.06 (s, 1H, ArH), 7.82 (brs, 7H, 7×OH); $\delta_C$ (125 MHz, acetone) 25.5, 46.6, 77.2, 95.0, 95.8, 99.2, 106.6, 113.5, 114.9, 117.9, 125.7, 130.6, 136.0, 144.6, 144.8, 145.1, 155.9, 156.7, 157.0, 166.2; MS (EI, m/z) 442 (M+1, 30%), 233 (M−208, 55%); HRMS (EI, m/z) found M 442.1126, $C_{22}H_{20}NO_9$ requires M 442.1138; $[\alpha]_D$ −319.0° (c 0.2, $CO(CH_3)_2$ at 26° C.

Example 2

Effect of Compound of Example 1 on MIC of Oxacillin for MRSA

The compounds were assayed in the following way:

Bacterial strains: *S. aureus* BB568 (COL-type strain that carries mecA and pT181) was provided by Professor B. Berger-Bächi. EMRSA-15 and EMRSA-16 were clinical isolates from the Royal Free Hospital, London.

Antibacterial susceptibility testing: Minimum Inhibitory Concentration (MIC) was determined by both broth and agar dilution techniques. Broth MIC testing was performed in 96-well microtitre trays with an inoculum of about $10^4$ cfu in 100 μL of Mueller-Hinton broth (MHB) (Oxoid, Basingstoke, United Kingdom) supplemented with 2% NaCl. MIC determinations by agar dilution were carried out using Mueller-Hinton agar (Oxoid) with an inoculum of about $10^4$ organisms per spot. For both methods, MIC values were obtained after incubation at 35° C. for 24 h. *S. aureus* ATCC29213 was used as the standard.

The assays yielded the following data:

TABLE 1

MIC of amide of example 1 and ECG in MHB + 2% NaCl at 35° C. after 24 hrs incubation

| Strain | MIC (mg/L) | |
|---|---|---|
| | Ex 1 | ECG |
| BB 568 | 128/256 | 256 |
| EMRSA 15 | 128/256 | 256 |
| EMRSA 16 | 128/128 | 128 |

TABLE 2

Effect of combination of amide of Example 1 & ECG on MIC of Oxacillin for MRSA

| Strain | MIC$^a$ mg/L | | | | |
|---|---|---|---|---|---|
| | — | Ex 1 12.5 mg/L | Ex 1 25 mg/L | ECG 12.5 mg/L | ECG 25 mg/L |
| BB 568 | 256/256 | 32/64 | 4/8 | 1 | ≦0.5 |
| EMRSA 15 | 32/32 | 1/1 | ≦0.5/0.5 | ≦0.5 | ≦0.5 |
| EMRSA 16 | 512/512 | 32/64 | 1/1 | 1 | ≦0.5 |

$^a$MIC of Oxacillin was determined in the absence (–) or presence of each compound at indicated concentrations. Cell growth was assessed after incubation at 35° C. for 24 h.

Example 3

Esterase Resistance of Compound of Example 1

The product of example 1 was tested for in esterase sensitivity as compared to ECG using commercially available porcine liver esterase (Sigma). ECG was totally hydrolysed to 10 min at 37° C. whereas the compound of example 1 was not affected in this time.

Example 4

Effect of ECg on Protein Export

This example examines the capacity of ECg and the novel amide of example 1 to modulate the export of proteins from *S. aureus*. *S. aureus* is grown in Mueller-Hinton broth containing various concentrates of ECg and amide of example 1. α-Toxin is detected in the growth medium by use of an anti-α-toxin antibody applied to exoproteins that are separated by SDS-PAGE and transferred to nitrocellulose membrane by electroblotting. The method will be used to determine the effect on export of DNase, alpha toxin, protein A and secreted β-lactamase. It is expected that the amide, as does ECg, will reduce the export of these proteins.

Example 5

Interaction of ECg and the Staphylococcal Membrane

The above observations are compatible with the concept that the compound exerts its effects through interaction with the cytoplasmic membrane of staphylococci, rather than through interaction with a specific target (such as peptidoglycan or the transcription regulatory system) on or within the bacterial cell.

This example investigates the capacity of the compound of example 1 and ECg to bind to staphylococcal cells: as shown in Table 3, the binding of ECg is enhanced by EC. It is expected that the binding of the amide of example 1 will be similarly enhanced. The method is based on Hashimoto, T. et al 1999.

TABLE 3

Influence of epicatechin (EC) on binding of epicatechin gallate (ECg) to EMRSA-16 cells

| Compound(s) added | Binding (%)$^a$ | | |
|---|---|---|---|
| | EC | ECg | EGCg |
| EC | 13.4 | — | — |
| Ecg | — | 22 | — |
| EGCg | — | — | 16.2 |
| EC + Ecg | 35.5 | 41.1 | — |
| Example 1 | | | |
| EC & Example 1 | | | |

$^a$Binding assessed by HPLC analysis of unbound catechin remaining in assay medium after cell removal.

Example 5

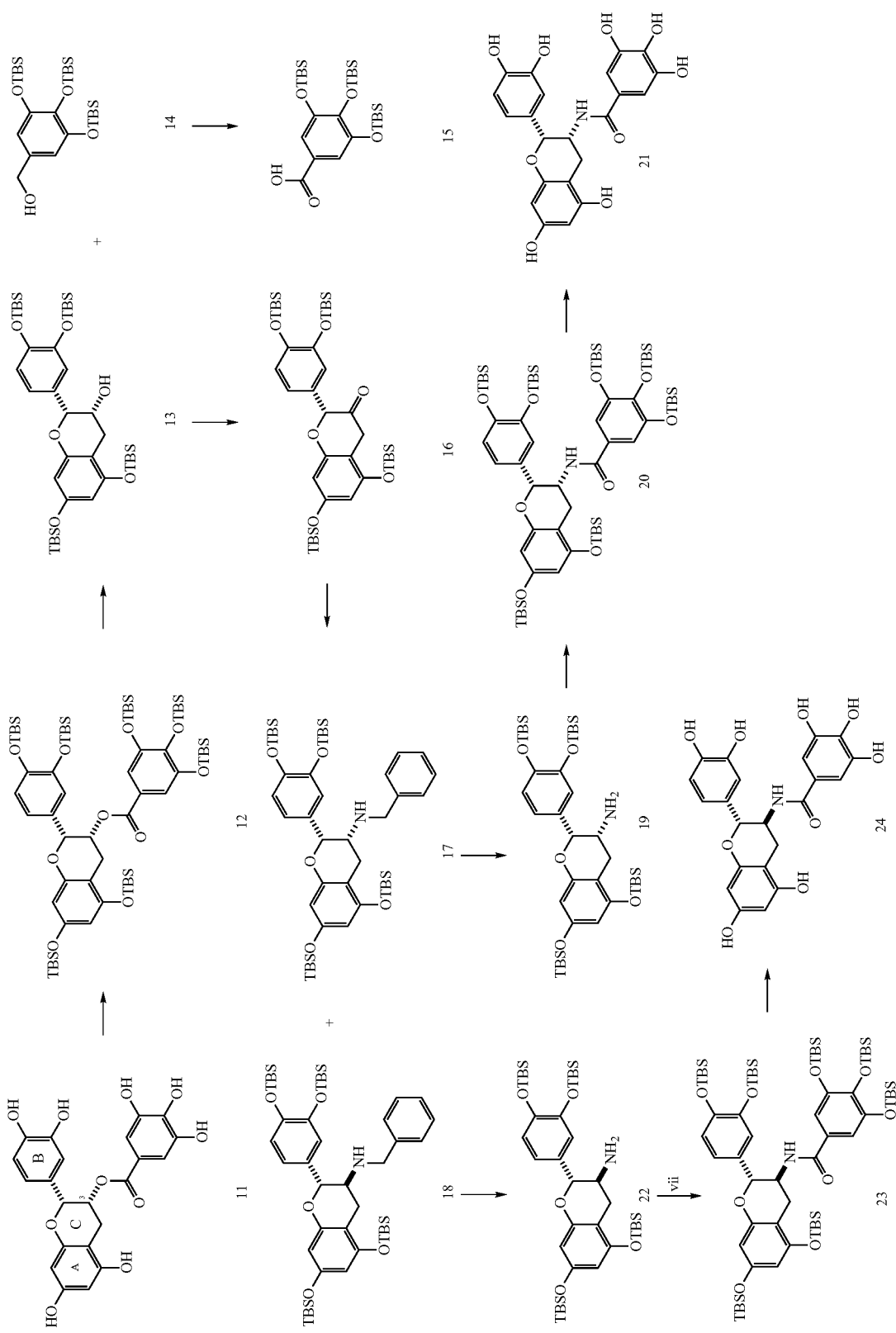

The steps to synthesise 12, 13, 16 and 18 were carried out as in Example 1 Compound 14 was isolated from the product mixture containing compound 13 by chromatography and it was present at a yield of 26%. To a solution of ketone 16 (500 mg, 0.67 mmol), in THF (10 mL) was added benzylamine (0.15 mL, 1.3 mmol) followed by acetic acid (3 drops) and the mixture was stirred for 30 minutes before the addition of sodium cyanoborohydride in THF (1M, 0.74 mL). The mixture was then stirred at room temperature overnight. The product was partitioned between ether (2×20 mL) and water (20 mL). The organics were then combined, dried with $MgSO_4$, filtered and concentrated in vacuo to yield a yellow oil which was purified by flash chromatography (eluting with 10% $Et_2O$: Pet Ether) to give:

Product 17 as a colorless oil, 250 mg, 45%; $v_{max}/cm^{-1}$ 2955, 2930, 2858; $\delta_H$ (400 MHz, $CDCl_3$) 0.16-0.27 (m, 24H, 4×$OSi(CH_3)_2C(CH_3)_3$), 0.99-1.29 (m, 36H, 4×$OSi(CH_3)_2C(CH_3)_3$), 2.70 (dd, 1H, J 17, 4.8, $ArCH_2CHCHO$), 2.78 (dd, 1H, J 17, 4.8, $ArCH_2CHCHO$), 3.21-3.23 (m, 1H, $ArCH_2CHCHO$), 3.71 (d, 1H, J 14, $NCH_2Ar$), 3.83 (d, 1H, J 14, $NCH_2Ar$), 5.09 (d, 1H, J 2.2, $ArCH_2CHCHO$), 5.99 (d, 1H, J 2.3, ArH), 6.14 (d, 1H, J 2.3, ArH), 6.84-6.93 (m, 3H, 3×ArH), 7.12-7.28 (m, 5H, 5×ArH); $\delta_C$ (125 MHz, $CDCl_3$) −3.9, −3.8, −3.7, −3.6, 18.6, 18.7, 18.9, 25.3, 26.2, 26.3, 26.4, 51.4, 53.1, 78.7, 101.8, 104.0, 105.6, 119.6, 119.7, 121.2, 127.1, 128.3, 128.6, 132.5, 146.6, 147.1, 155.2, 156.1; MS (FAB, m/z) 836 (M+1, 75%), 484 (M−351, 100%); HRMS (FAB, m/z) found M 836.4991, $C_{46}H_{78}NO_5Si_4$ requires M 836.4957; $[\alpha]_D$ −3.3° (c 1.0, $CH_2Cl_2$, at 23° C.);

Product 18 as a colorless oil, 68 mg, 26%; $v_{max}/cm^{-1}$ 2955, 2929, 2858; $\delta_H$ (400 MHz, $CDCl_3$) 0.18-0.28 (m, 24H, 4×$OSi(CH_3)_2C(CH_3)_3$), 0.98-1.06 (m, 36H, 4×$OSi(CH_3)_2C(CH_3)_3$), 2.50 (dd, 1H, J 15, 8.5, $ArCH_2CHCHO$), 2.96-3.07 (m, 3H, $ArCH_2CHCHO$ and $ArCH_2CHCHO$), 3.64 (d, 1H, J 14, $NCH_2Ar$), 3.83 (d, 1H, J 14, $NCH_2Ar$), 4.70 (d, 1H, J 7.6, $ArCH_2CHCHO$), 5.97 (d, 1H, J 2.3, ArH), 6.10 (d, 1H, J 2.4, ArH), 6.86-6.90 (m, 3H, 3×ArH), 7.15-7.31 (m, 5H, 5×ArH); $\delta_C$ (125 MHz, $CDCl_3$) −4.0, −3.8, −3.7, −3.6, 18.6, 18.7, 18.9, 26.0, 26.1, 26.2, 26.4, 51.1, 54.8, 81.4, 101.7, 104.0, 106.0, 120.3, 120.6, 127.4, 128.3, 128.8, 132.5, 147.4, 154.8, 155.2, 156.1; MS (FAB, m/z) 836 (M+1, 100%); HRMS (FAB, m/z) found M 836.4914, $C_{46}H_{78}NO_5Si_4$ requires M 836.4957; $[\alpha]_D$ +40.7° (c 0.1, $CH_2Cl_2$, at 25° C.).

A solution of amine 17 (420 mg, 0.51 mmol), was formed in EtOH (10 mL) and contacted with 5% palladium on activated carbon (10 mg) and the mixture was stirred vigorously under an atmosphere of hydrogen for 16 hours. The product was filtered through celite and concentrated in vacuo to yield a brown oil which was purified by flash chromatography (eluting with 20% $Et_2O$: Pet Ether) to give the product 19 as a colorless oil, 380 mg, 100%; $v_{max}/cm^{-1}$ 2956, 2929, 2858; $\delta_H$ (400 MHz, $CDCl_3$) 0.10-0.39 (m, 24H, 4×$OSi(CH_3)_2C(CH_3)_3$), 1.02-1.10 (s, 36H, 4×$OSi(CH_3)_2C(CH_3)_3$), 2.57-2.63 (m, 2H, $ArCH_2CHCHO$ and $NH_2$), 2.76-2.80 (m, 1H, $NH_2$), 2.89 (dd, 1H, J 16, 5.0, $ArCH_2CHCHO$), 3.29-3.31 (m, 1H, $ArCH_2CHCHO$), 5.17 (d, 1H, J 2.7, $ArCH_2CHCHO$), 6.06 (d, 1H, J 2.3, ArH), 6.19 (d, 1H, J 2.2, ArH), 6.88-6.97 (m, 3H, 3×ArH); $\delta_C$ (125 MHz, $CDCl_3$) −4.0, −3.8, −3.7, 1.4, 18.6, 18.7, 18.8, 26.1, 26.2, 26.3, 26.4, 42.1, 54.3, 78.5, 101.8, 103.9, 105.9, 119.5, 119.8, 121.1, 132.3, 146.6, 147.1, 155.1, 155.2 156.1; MS (FAB, m/z) 746 (M+1, 15%), 644 (M−101, 15%); HRMS (FAB, m/z) found M 746.4450, $C_{39}H_{72}NO_5Si_4$ requires M 746.4488; $[\alpha]_D$ −4.6° (c 4.0, $CH_2Cl_2$, at 25° C.).

Protected alcohol 14 was subjected to Dess-Martin Oxidation with periodinane in DCM at 0° C., then oxidised further with $NaO_2Cl$ in 2-methyl-2-butene and t-butanol in pH4 buffer at room temperature to form acid 15 at 58% yield.

To a solution of 15 (600 mg, 1.1 mmol), in DCM (10 mL) was added DCC (230 mg, 1.1 mmol) and DMAP (5 mg) and the mixture was stirred for 20 minutes. Amine 19 (670 mg, 0.92 mmol) was then added in DCM (5.0 mL) and the mixture was stirred at room temperature for 16 hours. The resulting precipitate was then filtered and the filtrate concentrated in vacuo to yield a yellow oil which was purified by flash chromatography (eluting with 20% $Et_2O$: Pet Ether) to give the product 20 as a colorless oil, 950 mg, 83%, containing small aromatic impurity; $v_{max}/cm^{-1}$ 2956, 2930, 2858, 1669, 1473; $\delta_H$ (500 MHz, $CDCl_3$) 0.18-0.31 (m, 42H, 7×$OSi(CH_3)_2C(CH_3)_3$), 0.99-1.09 (m, 63H, 7×$OSi(CH_3)_2C(CH_3)_3$), 3.03-3.04 (m, 2H, $ArCH_2CHCHO$), 4.89-4.91 (m, 1H, $ArCH_2CHCHO$), 5.18 (s, 1H, $ArCH_2CHCHO$), 6.09 (d, 1H, J 2.3, ArH), 6.20 (d, 1H, J 8.5, NH), 6.28 (d, 1H, J 2.3, ArH), 6.82 (s, 2H, 2×ArH), 6.89 (d, 1H, J 8.3, ArH), 6.98 (d, 1H, J 2.1, ArH), 7.04 (dd, 1H, J 8.3, 2.2, ArH); $\delta_C$ (100 MHz, $CDCl_3$) −3.9. −3.8, −3.7, −3.5, −3.4, −3.3, −3.2, 18.6, 18.7, 18.8, 19.0, 19.2, 26.1, 26.3, 26.5, 26.6, 28.0, 46.3, 77.7, 102.0, 104.9, 105.2, 108.9, 113.2, 116.4, 117.0, 119.1, 119.2, 120.9, 121.3, 125.2, 126.9, 129.0, 129.3, 131.4, 141.9, 144.0, 146.4, 146.9, 147.3, 148.8, 149.7, 155.5, 155.6, 155.8, 162.8, 166.6; MS (EI, m/z) 898 (M+1, 80%), 454 (M−444, 100%); HRMS (EI, m/z) found M not obtained; $[\alpha]_D$ −23.1° (c 2.5, $CHCl_3$, at 28° C.).

To a solution of amide 20 (110 mg, 0.13 mmol), in THF (2.0 mL) and pyridine (0.5 mL) and 0° C. was added HF.Py complex (0.5 mL). After 2 hours the reaction mixture was diluted with water (5 mL) and the product was extracted into EtOAc (2×10 mL). The organics were then combined, washed with saturated $CuSO_4$ (5 mL), dried with $MgSO_4$, filtered and concentrated in vacuo to yield a pale yellow solid which was purified by flash chromatography (eluting with 70% $Et_2O$: Pet Ether) to give the product 21 as a colorless oil 20 mg, 40%; $v_{max}/cm^{-1}$ 3320, 1604, 1516; $\delta_H$ (500 MHz, acetone) 2.87 (dd, 1H, J 16, 4.5, $ArCH_2CHCHO$), 3.01 (s superimposing dd, 2H, J 16, 5.2, NH and $ArCH_2CHCHO$), 4.76-4.79 (m, 1H, $ArCH_2CHCHO$), 5.27 (d, 1H, J 1.8, $ArCH_2CHCHO$), 6.06 (d, 1H, J 2.2, ArH), 6.12 (d, 1H, J 2.2, ArH), 6.82-6.93 (m, 4H, 4×ArH), 7.06 (s, 1H, ArH), 7.82 (brs, 7H, 7×OH); $\delta_C$ (125 MHz, acetone) 25.5, 46.6, 77.2, 95.0, 95.8, 99.2, 106.6, 113.5, 114.9, 117.9, 125.7, 130.6, 136.0, 144.6, 144.8, 145.1, 155.9, 156.7, 157.0, 166.2; MS (EI, m/z) 442 (M+1, 30%), 233 (M−208, 55%); HRMS (EI, m/z) found M 442.1126, $C_{22}H_{20}NO_9$ requires M442.1138; $[\alpha]_D$ −319.0° (c 0.2, $CO(CH_3)_2$ at 26° C.).

A solution of amine 18 (100 mg, 0.12 mmol), was formed in EtOH (10 mL) and contacted with 5% palladium on activated carbon (5.0 mg) and the mixture was stirred vigorously under an atmosphere of hydrogen for 16 hours. The product was filtered through celite and concentrated in vacuo to yield a yellow oil which was purified by flash chromatography (eluting with 50% $Et_2O$: Pet Ether) to give the product 22 as a colorless oil, 80 mg, 91%; $v_{max}/cm^{-1}$ 2956, 2929, 2858; $\delta_H$ (400 MHz, $CDCl_3$) 0.26-0.32 (m, 24H, 4×$OSi(CH_3)_2C(CH_3)_3$), 1.05 (s, 9H, $OSi(CH_3)_2C(CH_3)_3$), 1.06 (s, 9H, $OSi(CH_3)_2C(CH_3)_3$), 1.08 (s, 9H, $OSi(CH_3)_2C(CH_3)_3$), 1.09 (s, 9H, $OSi(CH_3)_2C(CH_3)_3$), 1.41 (brs, 2H, $NH_2$), 2.45 (dd, 1H, J 16, 9.8, $ArCH_2CHCHO$), 3.05 (dd, 1H, J 16, 5.4, $ArCH_2CHCHO$), 3.24-3.29 (m, 1H, $ArCH_2CHCHO$), 4.49 (d, 1H, J 6.8, $ArCH_2CHCHO$), 6.06 (d, 1H, J 2.2, ArH), 6.20 (d, 1H, J 2.3, ArH), 6.94-7.01 (m, 3H, 3×ArH); $\delta_C$ (125 MHz, $CDCl_3$) −4.0, −3.9, −3.7, −3.6, 18.6, 18.7, 18.8, 18.9, 26.1, 26.2, 26.3, 26.6, 41.4, 56.0, 81.2, 101.7, 104.1, 106.0, 120.2, 120.7, 121.6, 132.4, 147.4, 154.9, 155.2 156.1; MS (FAB, m/z) 746 (M+1, 20%), 367 (M−378, 100%); HRMS (FAB, m/z) found M 746.4568, C$_{39}$H$_{72}$NO$_5$Si$_4$ requires M 746.4488; [α]$_D$ +14.4° (c 4.0, CH$_2$Cl$_2$, at 25° C.).

Protected alcohol 14 was subjected to Dess-Martin Oxidation with periodinane in DCM at 0° C., then oxidised further with NaO$_2$Cl in 2-methyl-2-butene and t-butanol in pH4 buffer at room temperature to form acid 15 at 58% yield.

To a solution of 15 (90 mg, 0.20 mmol), in DCM (5.0 mL) was added DCC (42 mg, 0.20 mmol) and DMAP (5 mg) and the mixture was stirred for 20 minutes. Amine 22 (100 mg, 0.13 mmol) was then added in DCM (2.0 mL) and the mixture was stirred at room temperature for 16 hours. The resulting precipitate was then filtered and the filtrate concentrated in vacuo to yield a yellow oil which was purified by flash chromatography (eluting with 30% Et$_2$O: Pet Ether) to give the product 23 as a colorless oil, 90 mg, 59%; ν$_{max}$/cm$^{-1}$ 2929, 2858, 1582; δ$_H$ (400 MHz, CDCl$_3$) 0.09-0.26 (m, 24H, 4×OSi(CH$_3$)$_2$C(CH$_3$)$_3$), 0.84 (s, 9H, OSi(CH$_3$)$_2$C(CH$_3$)$_3$), 0.98 (s, 9H, OSi(CH$_3$)$_2$C(CH$_3$)$_3$), 1.00 (s, 9H, OSi(CH$_3$)$_2$C(CH$_3$)$_3$), 1.02 (s, 9H, OSi(CH$_3$)$_2$C(CH$_3$)$_3$), 2.53 (dd, 1H, J 17, 5.0, ArCH$_2$CHCHO), 2.70 (dd, 1H, J 17, 2.1, ArCH$_2$CHCHO), 4.72-4.76 (m, 1H, ArCH$_2$CHCHO), 5.30 (d, 1H, J 3.0, ArCH$_2$CHCHO), 6.03 (d, 1H, J 2.3, ArH), 6.19 (d, 1H, J 8.4, NH), 6.26 (d, 1H, J 2.3, ArH), 6.84-6.85 (m, 3H, 3×ArH), 6.99 (s, 2H, 2×ArH); δ$_C$ (125 MHz, CDCl$_3$) −4.4, −4.3, −4.2, −4.1, 18.3, 18.5, 22.1, 25.7, 25.8, 25.9, 46.9, 71.5, 75.2, 78.0, 101.4, 103.9, 104.1, 107.1, 118.2, 118.4, 121.2, 127.6, 128.1, 128.2, 128.6, 129.9, 132.3, 136.7, 137.5, 141.4, 147.0, 152.7, 154.6, 155.1, 155.5, 166.7; MS (EI, m/z) 1190 (M+Na, 50%), 589 (M−578, 100%); HRMS (EI, m/z) found M 1190.5826, C$_{67}$H$_{93}$NO$_9$NaSi$_4$ requires M 1190.5825.

To a solution of amide 23 (100 mg, 0.11 mmol), in THF (2.0 mL) and pyridine (0.5 mL) at 0° C. was added HF.Py complex (0.5 mL). After 2 hours the reaction mixture was diluted with water (5 mL) and the product was extracted into EtOAc (2×10 mL). The organics were then combined, washed with saturated CuSO$_4$ (5 mL), dried with MgSO$_4$, filtered and concentrated in vacuo to yield a pale yellow solid which was purified by flash chromatography (eluting with 70% Et$_2$O: Pet Ether) to give the product 24 as a colorless oil 20 mg, 45%; ν$_{max}$/cm$^{-1}$ 3275, 1521; δ$_H$ (500 MHz, acetone) 2.77 (dd, 1H, J 16, 3.3, ArCH$_2$CHCHO), 2.94 (dd, 1H, J 16, 5.5, ArCH$_2$CHCHO), 4.56-4.62 (m, 1H, ArCH$_2$CHCHO), 5.10 (d, 1H, J 7.7, ArCH$_2$CHCHO), 5.97 (d, 1H, J 2.2, ArH), 6.09 (d, 1H, J 2.2, ArH), 6.79-6.92 (m, 4H, 4×ArH), 7.00 (d, 1H, J 2.0, ArH), 7.39 (d, 1H, J 8.4, NH), 7.77-7.79 (m, 2H, 2×OH), 8.00-8.09 (m, 3H, 3×OH), 8.25 (s, 1H, OH); δ$_C$ (125 MHz, acetone) 25.0, 47.7, 79.4, 94.7, 95.4, 99.6, 106.7, 114.0, 118.9, 144.8, 145.1, 155.9, 156.4, 157.0; MS not obtained, several techniques attempted; [α]$_D$ +32.1° (c 1.0, CO(CH$_3$)$_2$ at 23° C.).

Example 6

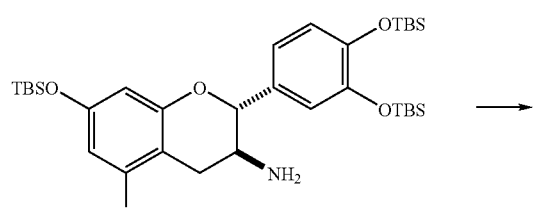

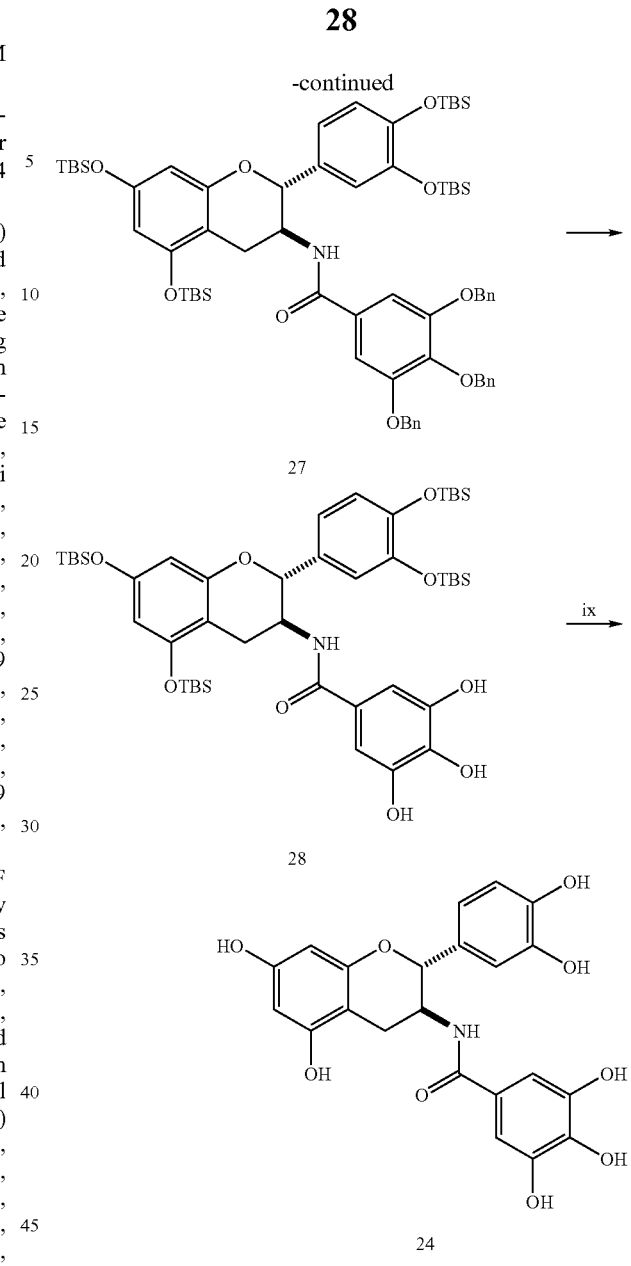

To a solution of tri-O-Bn gallic acid (90 mg, 0.20 mmol), in DCM (5.0 mL) was added DCC (42 mg, 0.20 mmol) and DMAP (5 mg) and the mixture was stirred for 20 minutes. Amine 22 synthesised as in example above (100 mg, 0.13 mmol) was then added in DCM (2.0 mL) and the mixture was stirred at room temperature for 16 hours. The resulting precipitate was then filtered and the filtrate concentrated in vacuo to yield a yellow oil which was purified by flash chromatography (eluting with 30% Et$_2$O: Pet Ether) to give the product 27 as a colorless oil, 90 mg, 59%; ν$_{max}$/cm$^{-1}$ 2929, 2858, 1582; δ$_H$ (400 MHz, CDCl$_3$) 0.09-0.26 (m, 24H, 4×OSi(CH$_3$)$_2$C(CH$_3$)$_3$), 0.84 (s, 9H, OSi(CH$_3$)$_2$C(CH$_3$)$_3$), 0.98 (s, 9H, OSi(CH$_3$)$_2$C(CH$_3$)$_3$), 1.00 (s, 9H, OSi(CH$_3$)$_2$C(CH$_3$)$_3$), 1.02 (s, 9H, OSi(CH$_3$)$_2$C(CH$_3$)$_3$), 2.53 (dd, 1H, J 17, 5.0, ArCH$_2$CHCHO), 2.70 (dd, 1H, J 17, 2.1, ArCH$_2$CHCHO), 4.72-4.76 (m, 1H, ArCH$_2$CHCHO), 5.11 (s, 2H, OCH$_2$Ph), 5.12 (s, 4H, 2×OCH$_2$Ph), 5.30 (d, 1H, J 3.0, ArCH$_2$CHCHO), 6.03 (d, 1H, J 2.3, ArH), 6.19 (d, 1H, J 8.4, NH), 6.26 (d, 1H, J 2.3, ArH), 6.84-6.85, (m, 3H, 3×ArH), 6.99 (s, 2H, 2×ArH), 7.27-7.42 (m, 15H, 15×ArH); $\delta_C$ (125 MHz, CDCl$_3$) −4.4, −4.3, −4.2, −4.1, 18.3, 18.5, 22.1, 25.7, 25.8, 25.9, 46.9, 71.5, 75.2, 78.0, 101.4, 103.9, 104.1, 107.1, 118.2, 118.4, 121.2, 127.6, 128.1, 128.2, 128.6, 129.9, 132.3, 136.7, 137.5, 141.4, 147.0, 152.7, 154.6, 155.1, 155.5, 166.7; MS (EI, m/z) 1190 (M+Na, 50%), 589 (M−578, 100%); HRMS (EI, m/z) found M 1190.5826, C$_{67}$H$_{93}$NO$_9$NaSi$_4$ requires M 1190.5825.

A solution of amide 27 (90 mg, 0.77 mmol) was formed in EtOH (5.0 mL) and there was added 5% palladium on activated carbon (5.0 mg) and the mixture was stirred vigorously under an atmosphere of hydrogen for 16 hours. The product was filtered through celite and concentrated in vacuo to yield a colorless oil which was purified by flash chromatography (eluting with 30% Et$_2$O: Pet Ether) to give the product 28 as a colorless oil, 48 mg, 69%; $\nu_{max}$/cm$^{-1}$ 3371, 2956, 2930, 2858; $\delta_H$ (400 MHz, CDCl$_3$) 0.04-0.26 (m, 24H, 4×OSi (CH$_3$)$_2$C(CH$_3$)$_3$), 0.89-1.02 (m, 36H, 4×OSi(CH$_3$)$_2$C(CH$_3$)$_3$), 2.12 (brs, 1H, OH), 2.55 (dd, 1H, J 17, 5.1, ArCH$_2$CHCHO), 2.71 (dd, 1H, J 17, 2.7, ArCH$_2$CHCHO), 4.67-4.73 (m, 1H, ArCH$_2$CHCHO), 5.30 (d, 1H, J 3.3, ArCH$_2$CHCHO), 6.01 (d, 1H, J 2.3, ArH), 6.23 (d, 1H, J 2.3, ArH), 6.47 (d, 1H, J 8.3, NH), 6.79-6.82 (m, 2H, 2×ArH), 6.90 (s, 2H, 2×ArH), 7.27 (brs, 2H, 2×OH); $\delta_C$ (100 MHz, CDCl$_3$) −3.9, −3.8, −3.7, −2.5, 18.6, 18.8, 26.1, 26.3, 47.7, 78.3, 101.8, 103.8, 104.4, 107.5, 118.5, 118.8, 121.6, 125.2, 132.5, 136.1, 144.7, 146.7, 147.4, 154.8, 155.4, 155.9, 168.7; MS (EI, m/z) 920 (M+Na, 25%), 898 (M+1, 100%); HRMS (EI, m/z) found M 898.4521, C$_{46}$H$_{76}$NO$_9$Si$_4$ requires M 898.4512; [α]$_D$ +4.4° (c 5.3, CHCl$_3$, at 28° C.).

Example 7

With the amide derivatives (21 and 24) in hand, their efficacy as modulators for β-lactam resistance in *S. aureus* was evaluated by determining their capcity to reduce the minimum inhibitory concentration (MIC) of oxacillin against MRSA strains BB 568, EMRSA-15 and EMRSA-16 as described in example 2.

The galloyl amides 21 and 24 possessed extremely weak intrinsic antibacterial activity against three MRSA strains: BB 568 and the two epidemic strains EMRSA-15 and EMRSA-16 (MIC mg/L, Table 4). This level of activity was comparable to that found with ECg. Sub-inhibitory concentrations (25 mg/L) of 21 were able to reduce the resistance to oxacillin of all three strains examined (oxacillin MIC mg/L, Table 4). In particular, oxacillin against BB 568 by 21 (from 256 mg/L to 4-8 mg/L) was less than that observed with ECg, but represented a very large diminution of sensitivity. Compound 24 was less effective that 21 with regard to its capacity to modify the sensitivity to oxacillin of BB 568 and EMRSA-16, although a significant degree of sensitisation was observed with MRSA-15 (Table 4).

The results show that sub-inhibitory concentrations (25 mg/L) of the amide analogue 21 possessing the natural C-3 stereochemistry, was able to reduce the resistance of three strains of methicillin resistant *S. aureus* (BB 568, EMRSA-15 and EMRSA-16) to oxacillin comparable to levels achieved with ECg. The higher activity of amide 21, compared to amide 24 indicates that carbonyl derived linkers demonstrating the natural 3R stereochemistry may provide compounds for improved sensitisation of MRSA isolates to a wide spectrum of β-lactam antibiotics.

TABLE 4

Antibacterial activity of ECg 21 and 24 and in combination with oxacillin against methicillin resistant *Staphylococcus aureus* (MRSA) strains

| MRSA strain | MIC (mg/L) | | | Oxacillin MIC (mg/L) | | | |
|---|---|---|---|---|---|---|---|
| | ECg | 21 | 24 | —[b] | ECg | 21[b] | 24[b] |
| BB 568 | 256 | 256 | 256 | 256/256 | ≦0.5 | 4/8 | 64/64 |
| EMRSA 15 | 256 | 256 | 256 | 32/32 | ≦0.5 | ≦0.5/≦0.5 | 2/4 |
| EMRSA 16 | 128 | 128 | 128 | 512/512 | ≦0.5 | 1/1 | 256/512 |

[b] results for 2 separate experiments given

Example 8

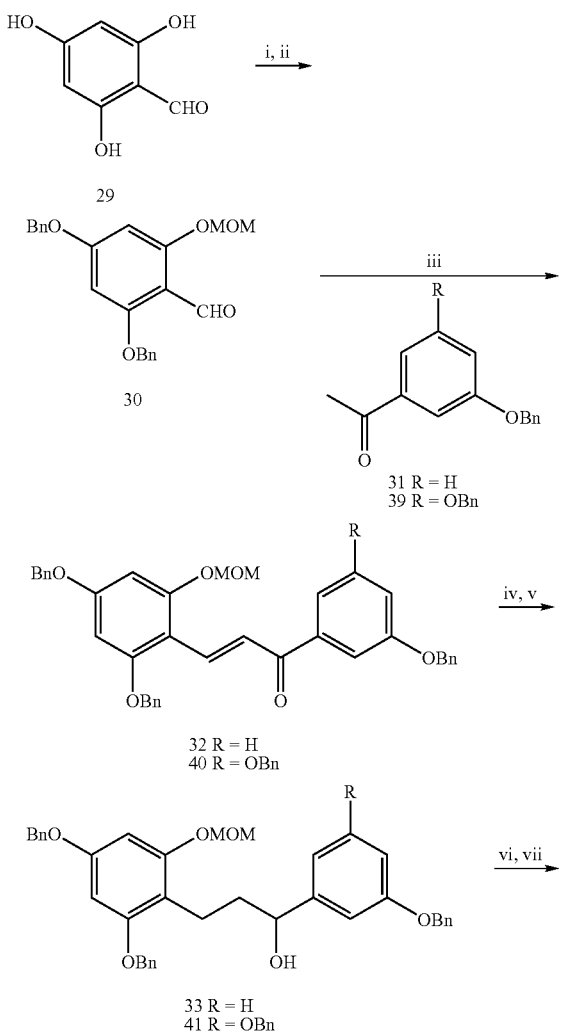

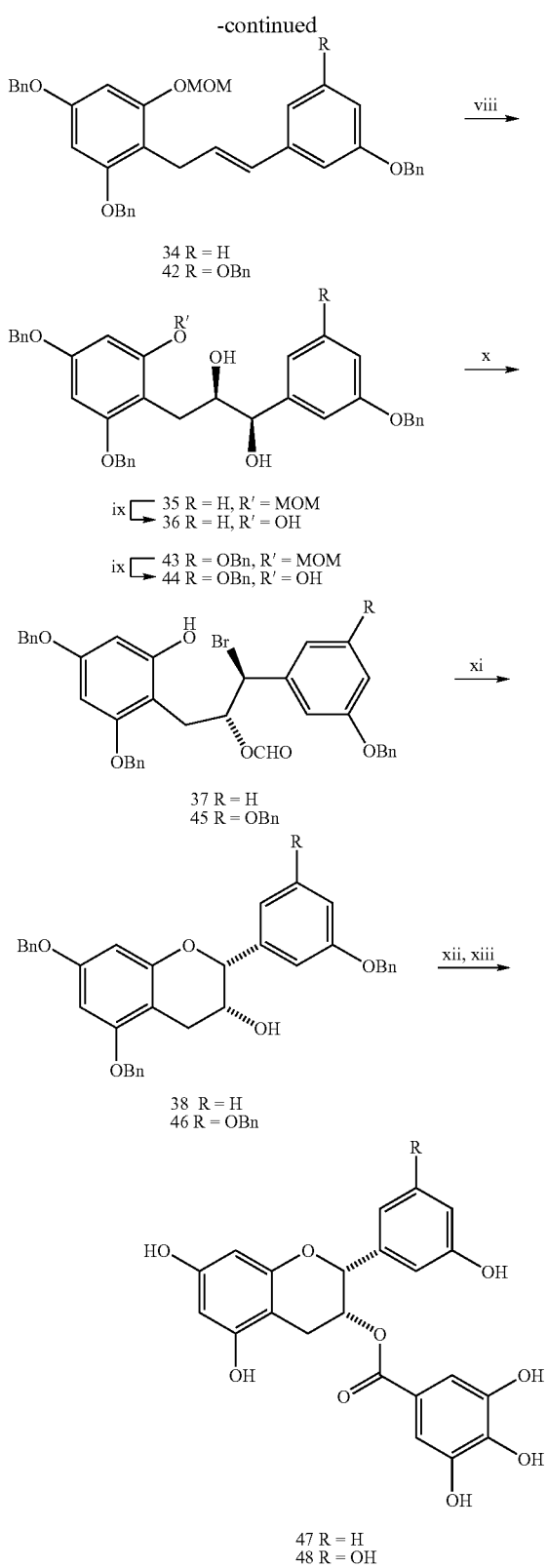

34 R = H
42 R = OBn

35 R = H, R' = MOM
36 R = H, R' = OH

43 R = OBn, R' = MOM
44 R = OBn, R' = OH

37 R = H
45 R = OBn

38 R = H
46 R = OBn

47 R = H
48 R = OH

Reagents: (i) $K_2CO_3$, BnBr, DMF, rt, 16 h, 69%; (ii) NaH, MOMCl, THF 0° C. to rt, 88%; (iii) KOH aq. (50%), EtOH, THF, rt, 16 h, R=H 69%, R=OBn 94%; (iv) Catechol borane, THF, −78° C. to rt, R=H 86% crude, R=OBn 86% crude; (v) $NaBH_4$, MeOH, rt, R=H 99% crude, R=OBn 99% crude; (vi) $PPh_3$, $Br_2$, $Et_3N$, $CH_2Cl_2$, 0° C. to rt, R=H 85%, R=OBn 99%; (vii) DBU, PhMe, 110° C., 16 h, R=H 57%, R=OBn 53%; (viii) AD-mix-β®, t-BuOH, $H_2O$, $MeSO_2NH_2$, 0° C., 5 days, R=H 65% @75% ee, 48% @>99% ee, R=OBn 82% @75% ee, 46% @>99% ee; (ix) HCl, MeOH, $Et_2O$, reflux, 5 h, R=H 100% crude, R=OBn 100% crude; (x) $HC(OMe)_3$, PPTS cat., $CH_2Cl_2$, rt; w/up then AcBr, $CH_2Cl_2$, rt, R=H 88% crude, R=OBn 91% crude; (xi) $K_2CO_3$, acetone, rt, 5 h; w/up then $K_2CO_3$, MeOH rt, 16 h, R=H 61%, R=OBn 45%; (xii) DCC, tri-OBn gallic acid, DMAP, $CH_2Cl_2$, rt, 16 h, R=H 64%, R=OBn 67%; (xiii) $H_2$, 10% $Pd(OH)_2/C$, EtOAc, rt, 12 h, R=H 94%, R=OH 37%.

4,6-Dibenzyloxy-2-O-methoxymethylbenzaldehyde (30). To a stirred solution of aldehyde 29 (5.0 g, 35 mmol) in DMF (50 mL) was added $K_2CO_3$ (9.7 g, 70 mmol) followed by BnBr (8.4 mL, 70 mmol) and the mixture was stirred at rt overnight. The mixture was then diluted with $Et_2O$ (100 mL) and washed with $H_2O$ (100 mL), dried ($MgSO_4$), filtered and concentrated in vacuo to yield a yellow solid which was recrystallised from $Et_2O$ to furnish the 4,6-dibenzyl protected aldehyde as a pale yellow semi-solid (8.1 g, 69%); IR $\nu_{max}$ 2922, 1635 $cm^{-1}$; 1H NMR (400 MHz, $CDCl_3$) d 5.04 (s, 2H, $OCH_2Ph$), 5.06 (s, 2H, $OCH_2Ph$), 6.14 (d, 1H, J 2.1, ArH) 6.17 (d, 1H, J 2.1, ArH), 7.37-7.50 (m, 10H, ArH), 10.24 (s, 1H, CHO); 13C NMR (100 MHz, $CDCl_3$) d 70.9, 80.1, 92.8, 94.6, 106.8, 127.5, 127.9, 128.0, 128.1, 128.8, 128.9, 129.0, 129.2, 129.3, 136.1, 163.1, 166.6, 166.8, 192.4; MS (ES, m/z) 334 ($M^+$, 20%), 91 ($Bn^+$, 100%); HRMS (ES, m/z) found 334.1215, $C_{21}H_{18}O_4$ requires 334.1205.

To a stirred solution of NaH (2.6 g, 66 mmol) in THF (100 mL) at 0° C. was added the 4,6-dibenzyl protected aldehyde (11 g, 33 mmol), in THF (30 mL). After 5 min. MOMCl (5.0 mL, 33 mmol) was added and the mixture allowed to warm to rt. Brine (5.0 mL) was then added and the reaction partitioned between $Et_2O$ (100 mL) and $H_2O$ (100 mL), the organic layer was dried ($MgSO_4$), filtered and concentrated in vacuo to yield aldehyde 30 as a brown oil (11 g, 88%); IR $\nu_{max}$ 3063, 3031, 2875 $cm^{-1}$; 1H NMR (400 MHz, $CDCl_3$) d 3.53 (s, 3H, $OCH_2OCH_3$), 5.09 (s, 2H, $OCH_2Ph$), 5.15 (s, 2H, $OCH_2Ph$), 5.27 (s, 2H, $OCH_2OCH_3$), 6.30 (d, 1H, J 2.1, ArH), 6.48 (d, 1H, J 2.1, ArH), 7.35-7.48 (m, 10H, ArH), 10.49 (s, 1H, CHO); 13C NMR (100 MHz, $CDCl_3$) d 56.9, 70.8, 71.0, 94.5, 95.1, 95.4, 110.5, 127.4, 127.5, 128.1, 128.4, 128.8, 128.9, 129.0, 129.1, 129.2, 136.2, 136.5, 161.8, 163.3, 165.3, 188.0; MS (ES, m/z) 378 ($M^+$, 10%), 91 ($Bn^+$, 100%); HRMS (ES, m/z) found 378.1456, $C_{23}H_{22}O_5$ requires 378.1467.

3',4,6-Tribenzyloxy-2-O-methoxymethyl-E-retro-chalcone (32). To a solution of acetophenone 31 (6.9 g, 32 mmol) in EtOH (100 mL) was added aq. KOH soltn. (10 mL of 50% m/v) and the mixture stirred at rt for 20 min. A solution of benzaldehyde 30 (11 g, 29 mmol) in THF (50 mL) was then added, and the mixture stirred overnight. The precipitate which had formed was then filtered and washed with $Et_2O$ to yield chalcone 32 (12 g, 69%), as a fine yellow powder; mp 108-10° C.; IR $\nu_{max}$ 3064, 3032, 2933, 1601, 1566, 1159 $cm^{-1}$; 1H NMR (500 MHz, $CDCl_3$) d 3.60 (s, 3H, $OCH_2OCH_3$), 5.16 (s, 2H, $OCH_2Ph$), 5.17 (s, 2H, $OCH_2Ph$), 5.19 (s, 2H, $OCH_2Ph$), 5.35 (s, 2H, $OCH_2OCH_3$), 6.46 (d, 1H, J 2.2, ArH), 6.62 (d, 1H, J 2.2, ArH), 7.19-7.21 (m, 1H, ArH), 7.28-7.30 (m, 2H, ArH), 7.42-7.57 (m, 15H, ArH), 7.66 (d, 1H, ArH), 7.99 (d, 1H, J 16, ArCH=CHCO), 8.41 (d, 1H, J 16, ArCH=CHCO); 13C NMR (100 MHz, $CDCl_3$) d 56.9, 70.5, 70.7, 71.4, 94.5, 94.9, 95.3, 108.2, 114.0, 119.9, 121.7, 122.5, 128.1, 128.5, 128.6, 128.7, 128.8, 129.0, 129.1, 129.3, 129.8, 136.2, 136.5, 136.7, 137.2, 140.9, 159.4, 159.9, 161.3, 162.5, 191.5; MS (ES, m/z) 586 (M+, 7%), 91 (Bn+, 100%); HRMS (ES, m/z) found 586.2340, $C_{38}H_{34}O_6$ requires 586.2355.

1-(3'-Benzyloxyphenyl)-3-(2"-O-methoxymethyl-4",6"-dibenzyloxyphenyl)propan-1-ol (33). Catechol borane (1M solution in THF, 10 mL, 10 mmol) was added dropwise to a stirred solution of chalcone 32 (5.0 g, 8.5 mmol) in THF (80 mL) at −78° C. The mixture was allowed to warm to rt and stirred for a further 1 h before acetone (10 mL) and sat. aq. NH$_4$Cl (10 mL) were added. The mixture was extracted into Et$_2$O (2×50 mL), the combined organic layers washed with 2M NaOH (50 mL) and brine (50 mL), then dried (MgSO$_4$) filtered, and concentrated in vacuo to afford the corresponding ketone (4.3 g, 86%). The crude ketone was immediately dissolved in methanol (30 mL) and NaBH$_4$ (310 mg, 8.0 mmol) was added at rt. The mixture was stirred for 1 h before all volatile material was removed in vacuo, H$_2$O (50 mL) added and the mixture extracted into Et$_2$O (3×30 mL). The combined organic layers were dried (MgSO$_4$) filtered, and concentrated in vacuo to give alcohol 11 (5.0 g, 99%) as a pale yellow solid; mp 120-2° C.; IR $\nu_{max}$ 3500, 2931, 1604 cm$^{-1}$; 1H NMR (400 MHz, CDCl$_3$) d 1.95-2.08 (m, 2H, ArCH$_2$CH$_2$CHOH), 2.90-2.92 (m, 2H, ArCH$_2$CH$_2$CHBr), 3.52 (s, 3H, OCH$_2$OCH$_3$), 4.61 (dd, 1H, J 8.8, 4.3, ArCH$_2$CH$_2$CHOH), 5.07 (s, 2H, OCH$_2$Ph), 5.08 (s, 2H, OCH$_2$Ph), 5.09 (s, 2H, OCH$_2$Ph), 5.23 (s, 2H, OCH$_2$OCH$_3$), 6.41 (d, 1H, J 2.2, ArH), 6.55 (d, 1H, J 2.2, ArH), 6.90 (ddd, 1H, J 8.2, 2.6, 0.8, ArH), 6.93 (d, 1H, J 8.2 ArH), 7.06 (apt, 1H, J 2.6, ArH), 7.26 (t, 1H, J 8.2 ArH), 7.35-7.50 (m, 15H, ArH); 13C NMR (100 MHz, CDCl$_3$) d 19.7, 39.3, 56.7, 70.3, 70.7, 70.9, 73.4, 94.8, 95.0, 95.3, 112.1, 112.8, 113.9, 118.9, 127.7, 128.0, 128.1, 128.3, 128.4, 128.5, 129.0, 129.1, 129.7, 137.3, 137.6, 146.9, 156.9, 158.3, 158.9, 159.3; MS (ES, m/z) 613 (M+$^+$Na, 80%), 523 (M$^+$−67, 100%); HRMS (ES, m/z) found 613.2578, $C_{38}H_{38}O_6Na$ requires 613.2566.

(E)-1-(3'-Benzyloxyphenyl)-3-(2"-O-methoxymethyl-4",6"-dibenzyloxyphenyl)propene (34). To a stirred solution of PPh$_3$ (1.4 g, 5.4 mmol) in CH$_2$Cl$_2$ (20 mL) at 0° C. was added Br$_2$ (0.30 mL, 5.4 mmol) dropwise and after 5 min, Et$_3$N (0.90 mL, 9.7 mmol) was added and the mixture stirred for a further 5 min. A solution of the alcohol 33 (2.1 g, 3.6 mmol) in CH$_2$Cl$_2$ (10 mL) was then added dropwise and the mixture allowed to warm to rt. After 2 h the mixture was concentrated in vacuo and purified by flash chromatography (neutral alumina, 50% Et$_2$O/hexanes) to afford the bromide as a yellow oil (2.0 g, 85%); IR $\nu_{max}$ 2931, 1594, 1150 cm$^{-1}$; 1H NMR (400 MHz, CDCl$_3$) d 2.50-2.58 (m, 2H, ArCH$_2$CH$_2$CHBr), 2.74-2.76 (m, 1H, ArCH$_2$CH$_2$CHBr), 2.89-2.93 (m, 1H, ArCH$_2$CH$_2$CHBr), 3.52 (s, 3H, OCH$_2$OCH$_3$), 5.05-5.09 (m, 7H, 3×OCH$_2$Ph and ArCH$_2$CH$_2$CHBr), 5.21 (dd, 2H, J 8.0, 6.7, OCH$_2$OCH$_3$), 6.37 (d, 1H, J 2.3, ArH), 6.53 (d, 1H, J 2.2, ArH), 6.89 (ddd, 1H, J 8.2, 2.5, 0.8, ArH), 7.00 (d, 1H, J 7.8 ArH), 7.07 (t, 1H, J 2.2, ArH), 7.20-7.23 (m, 1H, ArH), 7.33-7.47 (m, 15H, 15×ArH); 13C NMR (100 MHz, CDCl$_3$) d 22.5, 39.8, 56.0, 56.5, 56.6, 70.5, 70.6, 70.7, 94.6, 94.9, 95.1, 111.8, 114.7, 120.5, 127.6, 127.7, 127.9, 128.0, 128.1, 128.3, 128.5, 129.0, 130.0, 137.3, 137.4, 137.6, 144.3, 157.0, 158.3, 159.0, 159.3; MS (FAB, m/z) 654 (M$^+$, 100%); HRMS (FAB, m/z) found 654.1809, $C_{38}H_{37}O_5Br$ requires 654.1804.

A solution of bromide (3.3 g, 5.0 mmol) in DBU and toluene (25 mL, 4:1), was heated to reflux overnight. The mixture was then allowed to cool and extracted into Et$_2$O (3×25 mL). The combined organic layers were dried (MgSO$_4$), filtered and concentrated in vacuo. Purification by flash chromatography (Silica, 20% Et$_2$O/hexanes) gave styrene 34 (1.68 g, 57%) as a colorless oil; IR $\nu_{max}$ 3031, 2929, 1592 cm$^{-1}$; 1H NMR (400 MHz, CDCl$_3$) d 3.53 (s, 3H, OCH$_2$OCH$_3$), 3.63-3.64 (m, 2H, ArCH$_2$CH=CH), 5.08-5.10 (m, 2H, 3×OCH$_2$Ph), 5.24 (s, 2H, OCH$_2$OCH$_3$), 6.38-6.41 (m, 3H, ArCH$_2$CH=CH and ArH), 6.55 (d, 1H, J 2.3, ArH), 6.95-7.00 (m, 1H, ArH), 7.24 (t, 1H, J 4.3, ArH), 7.33-7.50 (m, 16H, ArH); 13C NMR (100 MHz, CDCl$_3$) d 27.0, 56.5, 70.3, 70.4, 70.7, 94.7, 95.0, 95.1, 110.9, 112.7, 113.6, 127.7, 127.9, 128.0, 128.1, 128.2, 128.3, 128.5, 129.0, 129.7, 129.8, 130.2, 137.4, 137.6, 140.1, 156.8, 158.3, 159.1, 159.4; MS (ES, m/z) 573 (M$^+$, 100%); HRMS (ES, m/z) found 573.2556, $C_{38}H_{37}O_5$ requires 573.2641.

(1R,2R)-1-(3'Benzyloxyphenyl)-3-(2"-O-methoxymethyl-4",6"-dibenzyloxyphenyl)propane-1,2-diol (13). To a solution of AD-mix-β® (5.0 g) in t-BuOH (30 mL) and H$_2$O (30 mL) at 0° C. was added methane sulfonamide (270 mg, 2.9 mmol) followed by styrene 34 (1.5 g, 2.6 mmol) in THF (30 mL) and the mixture stirred at 0° C. for 5 days. Solid sodium sulfite (5 g) was added and the product was extracted into EtOAc (3×30 mL), the combined organics dried (MgSO$_4$), filtered and concentrated in vacuo to yield the crude product which was purified by flash chromatography (Silica, 80% Et$_2$O/hexanes) to yield the desired product 35 as a white solid (1.0 g, 65%, 75% ee by HPLC24) that was then recrystallised (80% Et$_2$O/EtOAc) to give enantiomerically pure 35 (740 mg, 48%); mp 114-116° C.; IR $\nu_{max}$ 3405, 2964, 2923, 2851, 1605 cm$^{-1}$; 1H NMR (500 MHz, CDCl$_3$) d 2.60 (brs, 1H, OH), 2.97 (dd, 1H, J 14, 5.8, ArCH$_2$CH(OH)CH (OH)), 3.03 (dd, 1H, J 14, 8.1, ArCH$_2$CH(OH)CH(OH)), 3.36 (brs, 1H, OH), 3.53 (s, 3H, OCH$_2$OCH$_3$), 4.02-4.05 (m, 1H, ArCH$_2$CH(OH)CH(OH)), 4.60 (d, 1H, J 4.8, ArCH$_2$CH(OH) CH(OH)), 5.11-5.13 (m, 6H, 3×OCH$_2$Ph), 5.22 (dd, 2H, J 11, 6.7, OCH$_2$OCH$_3$), 6.47 (d, 1H, J 2.2, ArH), 6.58 (d, 1H, J 2.2, ArH), 6.98 (dd, 1H, J 8.2, 2.0, ArH), 7.03 (d, 1H, J 8.2, ArH), 7.15 (apt, 1H, J 2.0, ArH), 7.32 (t, 1H, J 8.2, ArH), 7.40-7.53 (m, 15H, ArH); 13C NMR (100 MHz, CDCl$_3$) d 27.9, 56.7, 70.4, 70.7, 71.0, 76.1, 76.7, 94.9, 95.1, 95.2, 108.7, 113.8, 114.3, 119.8, 127.7, 128.0, 128.1, 128.4, 128.5, 128.6, 129.0, 129.2, 129.7, 137.2, 137.5, 143.4, 157.2, 158.5, 159.3, 159.4; MS (ES, m/z) 629 (M+$^+$Na, 100%); HRMS (ES, m/z) found 629.2629, $C_{38}H_{38}O_7Na$ requires 629.2515; $[\alpha]_D$ +9.9° (c 0.1, CH$_2$Cl$_2$, at 21° C.).

(1R,2R)-1-(3'Benzyloxyphenyl)-3-(2"hydroxy-4",6"-dibenzyloxyphenyl)propane-1,2-diol (36). To a solution of diol 13 (740 mg, 1.2 mmol) in MeOH (10 mL) and Et$_2$O (10 mL) was added conc. HCl (5 drops) and the mixture heated at reflux for 5 h. The mixture was then concentrated in vacuo, diluted with EtOAc and washed with H$_2$O, the organic layer was dried (MgSO$_4$), filtered and concentrated in vacuo to yield the product 14 as a white solid (730 mg, 100%); mp 120-2° C.; IR $\nu_{max}$ 3436, 2923, 1739 cm$^{-1}$; 1H NMR (400 MHz, CDCl$_3$) d 2.81 (dd, 1H, J 15, 8.5, ArCH$_2$CH(OH)CH (OH)), 2.97 (dd, 1H, J 15, 3.8, ArCH$_2$CH(OH)CH(OH)), 4.00-4.04 (m, 1H, ArCH$_2$CH(OH)CH(OH)), 4.50 (d, 1H, J 6.3, ArCH$_2$CH(OH)CH(OH)), 4.90 (dd, 2H, J 14, 12, OCH$_2$Ph), 4.99-5.01 (m, 4H, OCH$_2$Ph), 6.26 (d, 1H, J 2.3, ArH), 6.31 (d, 1H, J 2.3, ArH), 6.88-6.92 (m, 1H, ArH), 6.99-7.00 (m, 1H, ArH), 7.17-7.20 (m, 2H, ArH), 7.33-7.47 (m, 15H, ArH); 13C NMR (100 MHz, CDCl$_3$) d 27.1, 70.4, 70.5, 77.2, 77.3, 93.9, 96.3, 106.7, 119.8, 127.2, 127.3, 128.0, 128.1, 128.4, 128.9, 129.0, 130.1, 137.3, 137.4, 142.6, 157.7, 158.3, 159.3, 159.5; MS (ES, m/z) 585 (M+$^+$Na, 40%), 563 (M$^+$, 100%); HRMS (ES, m/z) found 563.2358, $C_{36}H_{35}O_6$ requires 563.2434; $[\alpha]_D$ −15.6° (c 3.7, CH$_2$Cl$_2$, at 24° C.).

(1S,2R)-1-Bromo-2-formate (37). To a solution of triol 36 (730 mg, 1.3 mmol) in CH$_2$Cl$_2$ (15 mL) was added trimethyl orthoformate (1.4 mL, 13 mmol) followed by PPTS (5.0 mg) and the mixture stirred at rt for 10 min. The mixture was then washed with satd. aq. NaHCO$_3$ (10 mL), dried (MgSO$_4$), filtered and concentrated to in vacuo. The crude cyclic orthoformate was then redissolved in CH$_2$Cl$_2$ (15 mL), treated with AcBr (0.14 mL, 1.9 mmol) and stirred for 10 min at rt. The mixture was then washed with satd. aq. NaHCO$_3$ (10 mL) and concentrated in vacuo to afford bromo formate 37 as a brown foam (750 mg, 88%). This compound was used immediately without purification or characterization.

(2R,3R)-3'-Benzyloxy-4",6"-dibenzyloxyflavan (38). Crude bromo formate 37 (750 mg, 1.1 mmol) was treated with K$_2$CO$_3$ (170 mg, 1.1 mmol) in acetone (10 mL) and stirred at rt over 5 h. The mixture was diluted with H$_2$O (5.0 mL), extracted into EtOAc (3×10 mL), the combined organics dried with (MgSO$_4$), filtered and concentrated to dryness. The resulting compound was then redissolved in MeOH (10 mL), treated with K$_2$CO$_3$ (170 mg, 1.1 mmol) and the mixture stirred at rt overnight. The mixture was then concentrated in vacuo, extracted into EtOAc (3×15 mL), the combined organics dried (MgSO$_4$), filtered, concentrated to dryness and the product purified by flash chromatography (Silica, 50% Et$_2$O/ hexanes) to give 16 as a colorless oil (310 mg, 61%); IR $\nu_{max}$ 3439, 3031, 2924, 1619, 1592 cm$^{-1}$; 1H NMR (500 MHz, CDCl$_3$) d 3.06 (dd, 1H, J 17, 4.4, ArCH$_2$CHCHO), 3.11 (dd, 1H, J 9.8, 2.1, ArCH$_2$CHCHO), 4.39 (brs, 1H, ArCH$_2$CHCHO), 5.10-5.15 (m, 5H, ArCH$_2$CHCHO, and 2×OCH$_2$Ph), 5.19 (s, 2H, OCH$_2$Ph), 6.38 (d, 1H, J 2.3, ArH), 6.40 (d, 1H, J 2.3, ArH), 7.06 (dd, 1H, J 8.2, 2.5, ArH), 7.18 (dd, 1H, J 8.2, 0.6, ArH), 7.29 (s, 1H, ArH), 7.41-7.56 (m, 16H, ArH); 13C NMR (100 MHz, CDCl$_3$) d 28.3, 66.5, 69.9, 70.1, 70.2, 78.6, 94.2, 94.7, 101.0, 113.0, 114.4, 118.8, 127.2, 127.3, 127.7, 128.0, 128.1, 128.6, 128.7, 129.8, 136.9, 137.1, 139.9, 155.2, 158.4, 158.8, 159.1; MS (ES, m/z) 567 (M$^+$+Na, 20%), 545 (M$^+$, 100%); HRMS (ES, m/z) found 567.2111, C$_{36}$H$_{32}$O$_5$Na requires 567.2147; [α]$_D$ −25.7° (c 3.4, CH$_2$Cl$_2$, at 23° C.).

(−)-3-hydroxy B ring modified (−)-ECg (47). To a solution of gallic acid (54 mg, 0.12 mmol) in CH$_2$Cl$_2$ (5.0 mL) was added DCC (25 mg, 0.12 mmol) and the mixture was stirred at rt for 5 mins. Alcohol 38 (42 mg, 0.081 mmol) was then added in CH$_2$Cl$_2$ (5.0 mL) followed by DMAP (5.0 mg) and the mixture was stirred at rt overnight. The mixture was then filtered, concentrated in vacuo and purified by flash chromatography (Silica, 10% Et$_2$O/hexanes) to yield the globally protected gallate ester as a colorless oil (49 mg, 64%); IR $\nu_{max}$ 2923, 2851, 1707, 1590 cm$^{-1}$; 1H NMR (400 MHz, CDCl$_3$) d 3.19 (d, 2H, J 3.4, ArCH$_2$CHCHO), 4.82 (d, 1H, J 11, OCH$_2$Ph), 4.91 (d, 1H, J 11, OCH$_2$Ph), 5.08-5.10 (m, 11H, ArCH$_2$CHCHO, and 5×OCH$_2$Ph), 5.70-5.71 (m, 1H, ArCH$_2$CHCHO), 6.39 (d, 1H, J 2.3, ArH), 6.47 (d, 1H, J 2.3, ArH), 6.93 (dd, 1H, J 7.9, 2.2, ArH), 7.06 (d, 1H, J 7.9, ArH), 7.20-7.21 (m, 1H, ArH), 7.33-7.52 (m, 33H, ArH); 13C NMR (100 MHz, CDCl$_3$) d 26.5, 69.2, 70.4, 70.6, 71.4, 71.9, 75.0, 78.1, 94.4, 95.2, 101.4, 109.5, 110.6, 113.7, 114.9, 119.6, 127.7, 128.0, 128.1, 128.2, 128.4, 128.5, 128.6, 128.7, 129.0, 129.1, 129.9, 137.0, 137.3, 137.9, 139.9, 142.9, 152.8, 156.0, 158.5, 159.3, 165.6; MS (ES, m/z) 967 (M$^+$, 5%), 647 (M$^+$− 318, 100%); HRMS (ES, m/z) found 967.3859, C$_{64}$H$_{55}$O$_9$ requires 967.3846; [α]$_D$ −31.4° (c 3.3, CH$_2$Cl$_2$, at 23° C.).

A solution of the globally protected gallate ester (170 mg, 0.18 mmol) and 10% Pd(OH)$_2$ (10 mg) in EtOAc (10 mL) was stirred under an atmosphere of H$_2$ (balloon) for 12 h. The mixture was then filtered through celite, concentrated in vacuo and purified by flash chromatography (Silica, Et$_2$O) to yield the product (−)-47 as an off-white solid 72 mg, 94%; IR $\nu_{max}$ 3329 (br), 2950, 1607 cm$^{-1}$; 1H NMR (500 MHz, (CD$_3$)$_2$CO) d 2.99 (m, 1H, J 18, 2.0, ArCH$_2$CHCHO), 3.12 (dd, 1H, J 18, 4.6, ArCH$_2$CHCHO), 3.15 (brs, 1H, OH), 5.27 (s, 1H, ArCH$_2$CHCHO), 5.64-5.66 (m, 1H, ArCH$_2$CHCHO), 6.11 (d, 1H, J 2.3, ArH), 6.12 (d, 1H, J 2.3, ArH), 6.77 (ddd, 1H, J 8.0, 2.5, 0.9, ArH), 7.07-7.20 (m, 5H, ArH), 8.36 (brs, 5H, OH); 13C NMR (125 MHz, (CD$_3$)$_2$O) d 13.5, 68.4, 77.2, 94.4, 95.7, 98.0, 109.0, 113.9, 114.6, 117.7, 120.8, 129.0, 138.0, 140.4, 145.1, 156.0, 156.6, 157.0, 157.2, 165.1; MS (ES, m/z) 449 (M$^+$+Na, 65%), 257 (M$^+$−151, 100%); HRMS (ES, m/z) found 449.0818, C$_{22}$H$_{18}$O$_9$Na requires 449.0846; [α]$_D$ −130.8° (c 0.3, (CH$_3$)$_2$CO, at 23° C.).

3',4',5',6-Tetrabenzyloxy-2-O-methoxymethyl-E-retrochlacone, (40). Acetophenone 39 (3.3 g, 13 mmol) and benzaldehyde 30 (4.2 g, 11 mmol) were condensed in an identical manner to the preparation of 32 to give 40 (6.5 g, 94%), as a fine yellow powder; mp 108-10° C.; IR $\nu_{max}$ 2933, 2872, 1650, 1585, 1568, 1454 cm$^{-1}$; 1H NMR (400 MHz, CDCl$_3$) d 3.59 (s, 3H, OCH$_2$OCH$_3$), 5.09 (s, 4H, 2×OCH$_2$Ph), 5.16 (s, 2H OCH$_2$Ph), 5.20 (s, 2H, OCH$_2$Ph), 5.34 (s, 2H, OCH$_2$OCH$_3$), 6.28 (d, 1H, J 2.2, ArH), 6.60 (d, 1H, J 2.2, ArH), 6.84, (t, 1H, J 2.3, ArH), 7.23 (t, 1H J 2.3, ArH), 7.35-7.53 (m, 20H, ArH), 7.94 (d, 1H J 16, ArCH$_2$CH=CHCO), 8.41 (d, 1H J 16, ArCH$_2$CH=CHCO); 13C NMR (125 MHz, CDCl$_3$) d 56.1, 70.1, 70.3, 70.9, 94.4, 94.5, 94.7, 95.0, 106.9, 107.4, 107.7, 122.3, 126.7, 127.3, 127.5, 127.6, 127.7, 127.8, 128.1, 128.3, 128.7, 128.9, 136.1, 139.7, 159.5, 159.6, 160.7, 162.1, 191.4; MS (ES, m/z) 693 (M$^+$, 20%); HRMS (ES, m/z) found 693.2817, C$_{45}$H$_{41}$O$_7$ requires 693.2852.

1-(3',5'-Dibenzyloxyphenyl)-3-(2"-O-methoxymethyl-4", 6"-dibenzyloxyphenyl)propan-1-ol (41). In an identical manner to the preparation of 33 chalcone 40 (5.9 g, 9.5 mmol) was converted into crude ketone (4.7 g, 86%) and then alcohol 41 (4.7 g, 99%) as a pale yellow solid; mp 119-20° C.; IR $\nu_{max}$ 3575, 2946, 1594, 1497, 1453 cm$^{-1}$; 1H NMR (400 MHz, CDCl$_3$) d 1.99 (m, 2H, ArCH$_2$CH$_2$CHOH), 2.87 (m, 3H, ArCH$_2$CH$_2$CHOH and OH), 3.50 (s, 3H, OCH$_2$OCH$_3$), 5.02 (s, 4H, 2×OCH$_2$Ph), 5.07 (s, 2H, OCH$_2$Ph), 5.21 (s, 2H, OCH$_2$OCH$_3$), 6.37 (s, 1H, ArH), 6.57 (s, 2H, ArH), 6.68 (s, 2H, ArH), 7.24-7.47 (m, 20H, ArH); 13C NMR (100 MHz, CDCl$_3$) d.7, 39.2, 56.6, 70.5, 70.8, 73.5, 94.8, 95.0, 95.3, 101.1, 105.4, 112.0, 127.6, 128.0, 128.1, 128.3, 128.4, 128.5, 129.0, 129.1, 137.3, 147.8, 156.158.3, 160.3; MS (ES, m/z) 719 (M$^+$+Na, 30%), 239 (M$^+$−480, 100%); HRMS (ES, m/z) found 719.2916 C$_{45}$H$_{45}$O$_7$Na requires 719.2985.

(E)-1-(3',5'-Dibenzyloxyphenyl)-3-(2"-O-methoxymethyl-4",6"-dibenzyloxyphenyl)propene (42). In an identical manner to the preparation of 34 alcohol 41 (2.5 g, 4.0 mmol) gave the corresponding bromide (2.8 g, 99%) as a white solid; mp 114-5° C.; IR $\nu_{max}$ 3062, 2932, 1595, 1497, 1453 cm$^{-1}$; 1H NMR (400 MHz, CDCl$_3$) d 2.51 (m, 2H, ArCH$_2$CH$_2$CHBr), 2.78 (m, 1H, ArCH$_2$CH$_2$CHBr), 2.93 (m, 1H, ArCH$_2$CH$_2$CHBr), 3.52 (s, 3H, OCH$_2$OCH$_3$), 5.06 (m, 8H, 4×OCH$_2$Ph), 5.21 (s, 2H, OCH$_2$OCH$_3$), 6.36 (d, 1H, J 2.2, ArH), 5.85 (d, 1H, J 2.2, ArH), 6.59 (t, 1H, J 2.2, ArH), 6.75 (d, 2H, J 2.2, ArH), 7.33-7.53 (m, 20H, ArH); 13C NMR (100 MHz, CDCl$_3$) d 22.5, 39.7, 56.1, 56.6, 70.6, 94.7, 94.9, 95.2, 102.1, 107.2, 111.8, 127.4, 127.7, 128.0, 128.1, 128.2, 128.4, 128.5, 129.0, 137.2, 137.6, 145.0, 157.0, 158.3, 159.0, 160.4; MS (ES, m/z) 760 (M+, 10%), 723 (M+−37, 100%); HRMS (ES, m/z) found 760.2229, C$_{45}$H$_{44}$O$_6$Br requires 760.2222.

The bromide (2.8 g, 4.0 mmol) gave styrene 42 (1.3 g, 53%) as a white solid; mp 103-4° C.; IR $\nu_{max}$ 3087, 2932, 1676, 1593, 1497, 1453 cm$^{-1}$; 1H NMR (400 MHz, CDCl$_3$) d 3.53 (s, 3H, OCH$_2$OCH$_3$), 3.65-3.66 (m, 2H, CH$_2$CH=CH), 5.09 (s, 4H, 2×OCH$_2$Ph), 5.11 (s, 2H, OCH$_2$Ph), 5.14 (s, 2H, OCH$_2$Ph), 5.25 (s, 2H, OCH$_2$OCH$_3$), 6.37-6.38 (m, 2H, ArCH$_2$CH=CH), 6.42 (d, 1H, J 2.2, ArH), 6.54 (t, 1H, J 2.2, ArH), 6.57 (d, 1H, J 2.2, ArH), 6.64 (s, 1H, ArH), 6.65 (s, 1H, ArH), 7.34-7.56 (m, 20H, ArH); 13C NMR (100 MHz, CDCl$_3$) d 27.0, 56.6, 70.4, 70.5, 70.6, 70.7, 94.7, 95.0, 95.1, 101.1, 105.8, 108.3, 110.9, 127.6, 127.7, 128.0, 128.1, 128.3, 128.4, 128.5, 129.0, 129.1, 129.9, 130.5, 137.3, 137.4, 137.5, 137.7, 140.7, 156.9, 158.4, 159.1, 160.5; MS (ES, m/z) 679 (M$^+$, 10%), 576 (M$^+$–103, 100%); HRMS (ES, m/z) found 679.3167 C$_{45}$H$_{43}$O$_6$ requires 679.3060.

(1R,2R)-1-(3',5'-Dibenzyloxyphenyl)-3-(2"-O-methoxymethyl-4",6"-dibenzyloxyphenyl)propane-1,2-diol (43). In an identical manner to the preparation of 35 styrene 42 (1.4 g, 2.3 mmol) gave 43 as a white solid (1.2 g, 82%, 75% ee by HPLC24) that was then recrystallised (80% Et$_2$O/EtOAc) to give enantiomerically pure 43 (670 mg, 46%); mp 84-6° C.; IR v$_{max}$ 3520, 2928, 1594, 1151 cm$^{-1}$; 1H NMR (500 MHz, CDCl$_3$) d 2.99-3.10 (m, 2H, ArCH$_2$CH(OH)CH(OH)), 3.55 (s, 3H, OCH$_2$OCH$_3$), 4.06-4.09 (m, 1H, ArCH$_2$CH(OH)CH(OH)), 4.60 (d, 1H, J 4.5, ArCH$_2$CH(OH)CH(OH)), 5.11 (s, 4H, 2×OCH$_2$Ph), 5.13 (s, 2H, OCH$_2$Ph), 5.14 (s, 2H, OCH$_2$Ph), 5.25 (dd, 2H, J 13, 6.7, OCH$_2$OCH$_3$), 6.47 (d, 1H, J 2.2, ArH), 6.58 (d, 1H, J 2.2, ArH), 7.00 (t, 1H, J 2.1, ArH), 7.05 (s, 1H, ArH), 7.12 (s, 1H, ArH), 7.40-7.53 (m, 20H, ArH); 13C NMR (100 MHz, CDCl$_3$) d 27.6, 56.4, 70.1, 70.3, 70.6, 75.7, 76.2, 94.5, 94.7, 94.9, 101.2, 105.9, 108.3, 127.3, 127.8, 128.1, 128.2, 128.7, 128.9, 136.6, 136.8, 137.0, 143.9, 156.9, 158.1, 159.0, 160.0; MS (ES, m/z) 735 (M$^+$, 80%), 363 (M$^+$–372, 100%); HRMS (ES, m/z) found 735.2970, C$_{47}$H$_{43}$O$_8$ requires 735.2958; [α]$_D$ +3.0° (c 0.1, CH$_2$Cl$_2$, at 24° C.).

(1R,2R)-1-(3',5'-Dibenzyloxyphenyl)-3-(2"-hydroxy-4",6"-dibenzyloxyphenyl)propane-1,2-diol (44). In an identical manner to the preparation of 36 diol 43 (670 mg, 1.0 mmol) gave triol 42 as a white solid (600 mg, 100%); mp 91-2° C.; IR v$_{max}$ 3384, 3031, 2910, 1595, 1150 cm$^{-1}$; 1H NMR (400 MHz, CDCl$_3$) d 2.86 (dd, 1H, J 15, 12, ArCH$_2$CH(OH)CH(OH)), 3.01 (dd, 1H, J 15, 3.7, ArCH$_2$CH(OH)CH(OH)), 4.02-4.05 (m, 1H, ArCH$_2$CH(OH)CH(OH)), 4.50 (d, 1H, J 5.9, ArCH$_2$CH(OH)CH(OH)), 4.89-5.00 (m, 8H, 4×OCH$_2$Ph), 6.26 (d, 1H, J 2.3, ArH), 6.31 (d, 1H, J 2.3, ArH), 6.56 (t, 1H, J 2.1 ArH), 6.63 (s, 1H, ArH), 6.64 (s, 1H, ArH), 7.18-7.48 (m, 20H, ArH); 13C NMR (100 MHz, CDCl$_3$) d 27.2, 70.4, 70.5, 77.1, 94.0, 96.3, 102.3, 106.4, 106.7, 127.1, 128.0, 128.1, 128.4, 128.5, 128.9, 129.0, 129.1, 137.2, 137.4, 143.5, 157.6, 158.3, 159.5, 160.4; MS (ES, m/z) 669 (M$^+$, 100%); HRMS (ES) found 669.2855, C$_{43}$H$_{41}$O$_7$ requires 669.2852; [α]$_D$ –7.5° (c 4.2, CH$_2$Cl$_2$, at 24° C.).

(1S,2R)-1-Bromo-2-formate (45). In an identical manner to the preparation of 37 triol 44 (550 mg, 0.93 mmol) gave bromo formate 45 as a brown foam (580 mg, 91%). This compound was used immediately without purification or characterisation.

(2R,3R)-3',5'-Dibenzyloxy-4",6"-dibenzyloxyflavan (46). In an identical manner to the preparation of 38 crude bromo formate 45 (580 mg, 0.90 mmol) gave 46 as a colorless oil (222 mg, 45%); IR v$_{max}$ 3562, 3064, 3032, 2925, 1593, 1150 cm$^{-1}$; 1H NMR (400 MHz, CDCl$_3$) d 1.65 (d, 1H, J 5.2, OH), 2.87 (dd, 1H, J 18, 4.4, ArCH$_2$CHCHO), 2.97 (dd, 1H, J 18, 2.0, ArCH$_2$CHCHO), 4.19-4.23 (m, 1H, ArCH$_2$CHCHO), 4.86 (s, 1H, ArCH$_2$CHCHO), (d, 1H, J 11, OCH$_2$Ph), 4.88-5.02 (m, 8H, 4×OCH$_2$Ph), 6.21 (d, 1H, J 2.4, ArH), 6.23 (d, 1H, J 2.4, ArH), 6.53 (t, 1H, J 2.4, ArH), 6.70 (s, 1H, ArH), 6.71 (s, 1H, ArH), 7.21-7.30 (m, 20H, ArH); 13C NMR (100 MHz, CDCl$_3$) d 28.2, 66.5, 70.0, 70.2, 77.2, 78.6, 94.1, 94.7, 101.0, 101.6, 105.4, 127.2, 127.6, 127.9, 128.1, 128.5, 128.6, 136.7, 136.9, 137.0, 140.7, 155.1, 158.3, 158.8, 160.2; MS (ES, m/z) 651 (M$^+$, 80%), 225 (M–426, 100%); HRMS (ES, m/z) found 651.2741, C$_{43}$H$_{39}$O$_6$ requires 651.2747; [α]$_D$ –17.2° (c 0.8, CH$_2$Cl$_2$, at 24° C.).

(–)-3,5-dihydroxy B ring modified (–)-ECg (48). In an identical manner to the preparation of 47 alcohol 46 (100 mg, 0.17 mmol) was converted to the globally protected gallate ester (120 mg, 67%); IR v$_{max}$ 3063, 3031, 1714, 1593 cm$^{-1}$; 1H NMR (400 MHz, CDCl$_3$) d 3.03 (d, 2H, J 3.2, ArCH$_2$CHCHO), 4.65 (d, 1H, J 12, OCH$_2$Ph), 4.73 (d, 1H, J 12, OCH$_2$Ph), 4.86-5.10 (m, 13H, ArCH$_2$CHCHO, and 6×OCH$_2$Ph), 5.56-5.57 (m, 1H, ArCH$_2$CHCHO), 6.23 (d, 1H, J 2.4, ArH), 6.31 (d, 1H, J 2.4, ArH), 6.42 (t, 1H, J 2.0, ArH), 6.64 (s, 1H, ArH), 6.65 (s, 1H, ArH), 7.13-7.24 (m, 35H, ArH); 13C NMR (100 MHz, CDCl$_3$) d 26.5, 68.7, 70.0, 70.1, 70.2, 71.0, 75.1, 77.9, 94.0, 94.8, 101.0, 101.2, 106.0, 109.1, 125.1, 127.3, 127.5, 127.6, 127.7, 127.8, 127.9, 128.0, 128.2, 128.4, 128.6, 136.6, 136.7, 136.9, 137.5, 138.1, 142.6, 152.4, 155.6, 158.0, 158.9, 160.0, 165.1; [α]$_D$ –43.8° (c 2.4, CH$_2$Cl$_2$, at 24° C.).

A solution of the globally protected gallate ester (120 mg, 0.11 mmol) was hydrogenolysed to give (–)-48 as an off-white solid (18 mg, 37%); IR v$_{max}$ 3332, 1608, 1237 cm$^{-1}$; 1H NMR (400 MHz, (CD$_3$)$_2$CO) d 2.76-2.95 (m, 2H, ArCH$_2$CHCHO), 4.99 (s, 1H, ArCH$_2$CHCHO), 5.46-5.48 (m, 1H, ArCH$_2$CHCHO), 5.91-5.93 (m, 2H, ArH), 6.11 (t, 1H, J 2.4, ArH), 6.43-6.44 (m, 2H, ArH), 6.88 (s, 2H, ArH), 8.01 (brs, 7H, OH); 13C NMR (100 MHz, (CD$_3$)$_2$O) d 20.7, 26.6, 60.8, 66.6, 69.2, 78.1, 95.8, 96.6, 99.1, 102.8, 106.0, 110.0, 121.8, 138.8, 139.0, 141.0, 146.0, 156.9, 157.5, 157.8, 159.2, 166.1; MS (ES, m/z) 443 (M$^+$, 80%), 273 (M$^+$–169, 100%); HRMS (ES, m/z) found 443.1017, C$_{22}$H$_{19}$O$_{10}$ requires 443.0978; [α]$_D$ –55° (c 2.5, (CH$_3$)$_2$O, at 24° C.).

Example 9

Microbiological Evaluation

With the B-ring modified analogues 47 and 48 in hand, their efficacy as modulators for β-lactam resistance in *S. aureus* was evaluated by determining their capacity to reduce the minimum inhibitory concentration (MIC) of oxacillin against MRSA strains BB 568, EMSRA-15 and EMSRA-16 (Table 5)

TABLE 5

Antibacterial activity of ECg, 47 and 48 in combination with MRSA strains

| MRSA Strain | MIC (mg/L) | | |
|---|---|---|---|
| | ECg | 47 | 48 |
| B B 568 | 256 | >128 | 128 |
| EMRSA-15 | 256 | >128 | 64 |
| EMRSA-16 | 128 | 128 | 32 |

[a] MICs were determined in Mueller-Hinton Broth + 2% salt at 35° C. after 24 h incubation.

The monohydroxylated B-ring analogue 47 possessed little or no intrinsic antibacterial activity against the three MRSA strains and in this respect was comparable to ECg (Table 5). Interestingly, the 3,5-dihydroxy B-ring analogue 48 showed weak to moderate anti-staphylococcal activity that was significantly higher than that shown by ECg and analogue 47 suggesting that the position of hydroxyl groups on the B-ring may influence the intrinsic antibacterial activity of ECg analogues. Sub-inhibitory concentrations (6.25, 12.5 and 25 mg/L) of both compounds were effective in reducing the MIC of all three strains examined.

TABLE 6

Compound: ECg

| MRSA Strain | Oxacillian MIC[b] (mg/L) | | | |
|---|---|---|---|---|
| | — | 6.25 mg/L | 12.5 mg/L ECg | 25 mg/L ECg |
| BB568 | 256 | 1 | ≦0.5 | ≦0.5 |
| EMRSA-15 | 32 | ≦0.5 | ≦0.5 | ≦0.5 |
| EMSRA-16 | 512 | ≦0.5 | ≦0.5 | ≦0.5 |

[b]Fixed concentrations of the compound were used (6.25, 12.5 and 25 mg/L)

TABLE 7

Compound 47

| MRSA Strain | Oxacillin (MICb (mg/L) | | | |
|---|---|---|---|---|
| | — | 6.25 mg/L | 12.5 mg/L | 25 mg/L |
| BB568 | 256 | 16 | 2 | ≦0.5 |
| EMSRA-15 | 32 | 2 | ≦0.5 | ≦0.5 |
| EMSRA-16 | 512 | 32 | 1 | ≦0.5 |

TABLE 8

Compound 48

| MRSA Strain | Oxacillin MICb (Mg/L) | | | |
|---|---|---|---|---|
| | — | 6.25 mg/L | 12.5 mg/L | 25 mg/L |
| BB568 | 256 | 16 | 1 | ≦0.5 |
| EMSRA-15 | 32 | 2 | ≦0.5 | ≦0.5 |
| EMSRA-16 | 512 | 64 | ≦0.5 | ≦0.5 |

At a concentration of 25 mg/L, ECg and the two analogues (47 and 48) fully sensitised each of the three MRSA strains to oxacillin, reducing the MICs to less than 0.5 mg/L, a figure well below the clinically-relevant breakpoint for β-lactam antbiotics. At 6.25 mg/L of catechin gallate, the lowest concentration used in this study, both the monohydroxylated B-ring analogue and the 3,5-dihydroxy B-ring analogue were less potent than the natural compound.

REFERENCES

Cartula, N, Vera-Samper, E, Villalain, J, Reyes Mateo, C & Micol, V. (2003) The relationship between the antioxidant and the antibacterial properties of glloylated catechins and the structure of phospholipid model membranes. Free Rad. Biol. Med. 34:648-662.

Hamilton-Miller, J M T & Shah, S. (1999) Disorganization of cell division of methicillin-resistant *Staphylococcus aureus* by a component of tea (*Camellia sinensis*): a study by electron microscopy. FEMS Microbiol. Lett. 176:463-469.

Hashimoto, T, Kumazawa, S, Nanjo, F, Hara, Y & Nakayama, T. (1999) Interaction of tea catechins with lipid bilayers investigated with liposome systems. Biosci. Biotechnol. Biochem. 63:2252-2255.

Kajiya, K, Kumazawa, S & Nakayama, T. (2001) Steric effects on interaction of tea catechins with lipid bilayers. Biosci. Biotechnol. Biochem. 65:2638-2643.

Kajiya, K, Kumazawa, S & Nakayama, T. (2002) Effects of external factors on the interaction of tea catechins with lipid bilayers. Biosci. Biotechnol. Biochem. 66:2330-2335.

Kohri, T., Matsumoto, N., Yamakawa, M., Suziki, M., Nanjo, F., Hara, Y., Oku, N. (2001) Metabolic fate of (−)-(4-3H) epigallocatechin gallate in rats after oral administration. J. Agricul. & Food chem., 49: 4102-4112.

Nakayama, T, Ono, K & Hashimoto, K. (1998) Affinity of antioxidative polyphenols for lipid bilayers evaluated with a liposme system. Biosci. Biotechnol. Biochem. 62:1005-1007.

Stapleton, P D & Taylor, P W. (2002) Methicillin resistance in *Staphylococcus aureus*: mechanisms and modulation. Sci. Progr. 85:57-72.

Stapleton, P D, Shah, S, Anderson, J C, Hara, Y, Hamilton-Miller, J M T & Taylor, P W. (2004) Modulation of β-lactam resistance in *Staphylococcus aureus* by catechins and gallates. Int. J. Antimicrob. Agents, 2315 23: 462-7.

Yam, T S, Shah, S & Hamilton-Miller, J M T. (1997) Microbiological activity of whole and fractionated crude extracts of tea (*Camellia sinensis*), and of tea components. FEMS Microbiol. Lett. 152:169-174.

Yam, T S, Hamilton-Miller, J M T & Shah, S. (1998) The effect of a component of tea (*Camellia sinensis*) on methicillin resistance, PBP2' synthesis, and β-lactamase production in *Staphylococcus aureus*. J. Antimicrob. Chemother. 42:211-216.

Yamashita, S., Yokoma, K., Matsumiya, N. & Yamaguchi, H. (2001) Successful green tea nebulization therapy for subglottic tracheal stenosis due to MRSA infection, *J. Infect.*, 42:222-223.

The invention claimed is:

1. A compound of the formula I

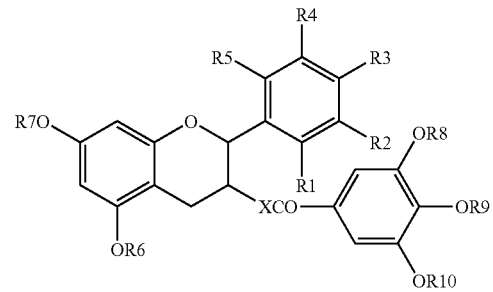

Formula 1 in which $R^8$ to $R^{10}$ are individually selected from the group consisting of hydrogen, aryl, $C_{1-6}$ alkyl, trialkylsilyl and acyl;

$R^1$ to $R^5$ are selected from hydrogen or hydroxyl;

$R^6$ and $R^7$ are each selected from the group consisting of H, $C_{1-4}$ alkyl, trialkylsilyl and acyl;

X is O or NR, and R is H or Me;

in which any of the alkyl groups including alkyl groups in alkoxy, acyl and acyloxy groups may be substituted by one or more aryl, $C_{1-4}$ alkyl, $C_{1-4}$ alkoxy, hydroxyl, trialkylsiloxy or acyloxy groups;

and wherein (I) $R^2$ is OH, and in which $R^4$ is H or OH and $R^1$, $R^3$ and $R^5$ are H; or (II) $R^3$ is OH and the remainder of $R^1$-$R^5$ are H; or (III) four of $R^1$-$R^5$ are OH.

2. The compound according to claim 1 in which $R^2$ is OH, $R^4$ is H or OH and $R^1$, $R^3$ and $R^5$ are H.

3. The compound according to claim 1 in which $R^3$ is OH and the remainder of $R^1$-$R^5$ are H.

4. The compound according to claim 1 in which four of $R^1$-$R^5$ are OH.

5. A compound according to claim 1 in which X is O.

6. The compound according to claim 1 in which X is NR.

7. The compound according to claim 6 in which R is H.

8. The compound according to claim 1 in which each of $R^8$, $R^9$ and $R^{10}$ is H.

9. The compound according to claim 1 in which $R^6$ and $R^7$ are H.

10. The compound according to claim 1 which has the structure Ia or

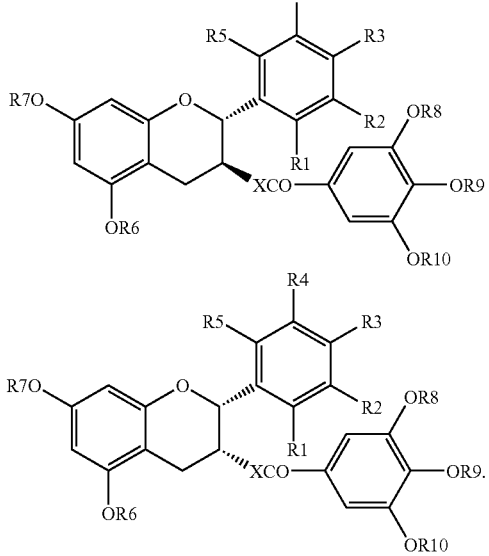

11. The compound according to claim 10 which has formula Ib.

12. The compound according to claim 10 wherein X is NR.

13. The compound according to claim 11 wherein X is NR.

14. A method of treatment of methicillin resistant *S. aureus* infection in a human in which a compound according to claim 1 is administered to the human.

15. Method according to claim 14 in which a β-lactam antibiotic is also administered to the human in the treatment.

16. A pharmaceutical composition comprising a compound as claimed in claim 1 and a carrier.

17. A pharmaceutical composition comprising the compound of claim 1 and a pharmaceutical excipient.

18. The composition according to claim 17 further comprising a β-lactam antibiotic.

19. A method of synthesising an ester or amide product in which a compound of the formula II

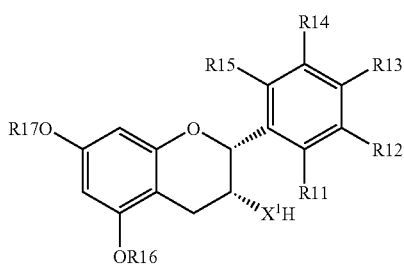

in which $X^1$ is O or $NR^{21}$; $R^{11}$-$R^{15}$ are either H or $OR^{22}$; $R^{21}$ is H or Me; each $R^{22}$ is a hydroxyl protecting group; and $R^{16}$ and $R^{17}$ are each a hydroxyl protecting group, is reacted with an acylating compound of the formula III

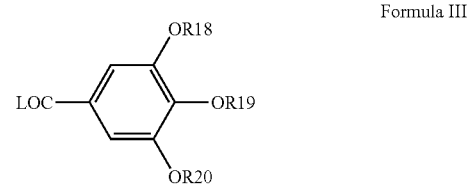

in which each of $R^{18}$, $R^{19}$ and $R^{20}$ is a hydroxyl protecting group and L is a leaving group to produce a compound of the formula IV

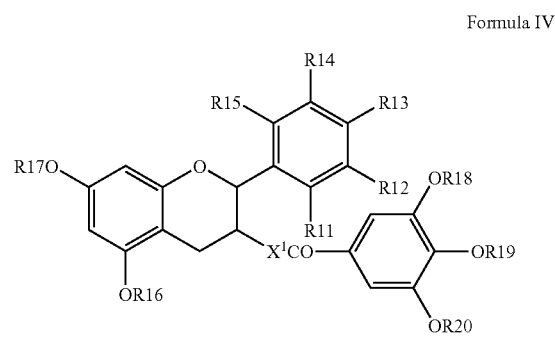

in which $X^1$ and $R^{11}$-$R^{20}$ have the same meanings as in the compound of the formula II and the compound of the formula III;

and wherein (I) $R^{12}$ is $OR^{22}$, $R^{14}$ is H or $OR^{22}$ and $R^{11}$, $R^{13}$ and $R^{15}$ are H; or (II) $R^{13}$ is $OR^{22}$ and the remainder of $R^{11}$-$R^{15}$ are H; or (III) four of $R^{11}$-$R^{15}$ are $OR^{22}$.

20. The method according to claim 19 in which the compound of formula IV is subjected to one or more hydroxyl deprotection steps in which some or all of the groups $R^{16}$-$R^{20}$ are replaced by hydrogen and any of $R^{11}$-$R^{15}$ which are $OR^{22}$ are replaced by OH.

21. The method according to claim 19 in which $X^1$ is O.

22. The method according to claim 19 in which $X^1$ is $NR^{21}$.

23. The method according to claim 22 in which $R^{21}$ is hydrogen and in which the compound of formula IV is methylated with a methylating reagent to replace the N-hydrogen atom of $X^1$ by a methyl group, to produce a final compound having formula IV in which $X^1$ is NMe.

24. The method according to claim 22 including a preceding step of producing the compound of formula II wherein X is $NR^{21}$ by reductive amination of a compound of the formula V

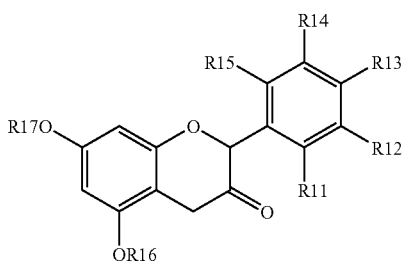

Formula V in which the groups $R^{11}$ to $R^{17}$ have the same meanings as in the compound II with an amine reagent of general formula VI $H_2NR^{23}$  VI in which $R^{23}$ is hydrogen, an alkyl group or an aralkyl group, and a reducing agent to produce a compound of formula VII

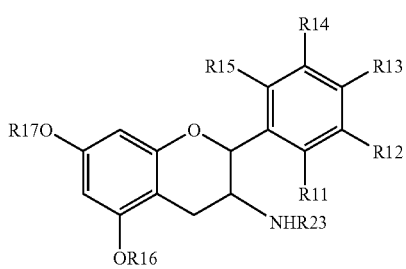

Formula VII in which $R^{11}$ to $R^{17}$ and $R^{23}$ have the same meanings as in the respective starting compounds.

25. The method according to claim 24 in which $NR^{23}$ in the compound of formula VII is different to $NR^{21}$ in the amine compound of the formula II which includes the step of replacing the group $R^{23}$ of the compound of the formula VII by a group $R^{21}$ which is a hydrogen atom or a methyl group prior to the reaction of II with acylating compound of the formula III.

26. The method according to claim 25 in which $R^{23}$ is benzyl.

27. The method according to claim 24 which includes a further preceding step in which the compound of formula V is produced by oxidation of an alcohol compound of the formula VIII

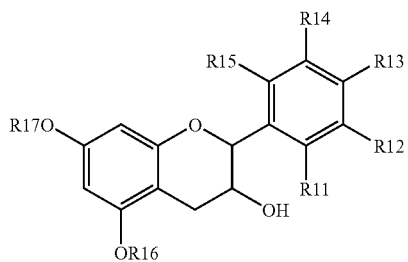

Formula VIII in which $R^{11}$ to $R^{17}$ have the same meanings as in the compound of formula V, using an oxidising agent.

28. The method according to claim 27 in which the oxidising agent is Dess-Martin periodinane.

* * * * *